(12) United States Patent
Rumberger et al.

(10) Patent No.: US 9,464,262 B2
(45) Date of Patent: *Oct. 11, 2016

(54) INTERCALATED BLEACH COMPOSITIONS, RELATED METHODS OF MANUFACTURE AND USE

(71) Applicant: THE CLOROX COMPANY, Oakland, CA (US)

(72) Inventors: Evan Rumberger, Pleasanton, CA (US); Marisa MacNaughtan, Pleasanton, CA (US); William L. Smith, Pleasanton, CA (US); Kelsey Kornaus, Durham, NC (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,268

(22) Filed: May 10, 2016

(65) Prior Publication Data

US 2016/0251601 A1      Sep. 1, 2016

Related U.S. Application Data

(63) Continuation of application No. 14/724,349, filed on May 28, 2015, now Pat. No. 9,353,336, which is a continuation of application No. 14/050,085, filed on Oct. 9, 2013, now Pat. No. 9,074,164.

(51) Int. Cl.

| | |
|---|---|
| *C11D 1/00* | (2006.01) |
| *C11D 3/02* | (2006.01) |
| *C11D 3/395* | (2006.01) |
| *C11D 3/08* | (2006.01) |
| *C11D 3/12* | (2006.01) |
| *C11D 3/04* | (2006.01) |
| *C11D 3/37* | (2006.01) |
| *C11D 17/06* | (2006.01) |
| *C11D 17/00* | (2006.01) |
| *C11D 3/10* | (2006.01) |

(52) U.S. Cl.
CPC ............. *C11D 3/3953* (2013.01); *C11D 1/00* (2013.01); *C11D 3/04* (2013.01); *C11D 3/042* (2013.01); *C11D 3/044* (2013.01); *C11D 3/046* (2013.01); *C11D 3/08* (2013.01); *C11D 3/10* (2013.01); *C11D 3/12* (2013.01); *C11D 3/1213* (2013.01); *C11D 3/3757* (2013.01); *C11D 3/3956* (2013.01); *C11D 17/0073* (2013.01); *C11D 17/06* (2013.01)

(58) Field of Classification Search
CPC ............ C11D 1/00; C11D 3/04; C11D 3/10; C11D 3/12; C11D 3/044; C11D 3/046; C11D 3/3953; C11D 3/3956; C11D 17/06; C11D 17/0073
USPC ........ 510/302, 303, 380, 445, 446, 435, 509
See application file for complete search history.

(56) References Cited

U.S. PATENT DOCUMENTS

| | | | | |
|---|---|---|---|---|
| 1,400,167 | A | 12/1921 | Kereszty et al. | |
| 1,878,510 | A | 9/1932 | Mindeleff | |
| 3,582,265 | A | 6/1971 | Bishop et al. | |
| 4,071,605 | A | 1/1978 | Wojtowicz | |
| 4,108,792 | A | 8/1978 | Farmer, Jr. et al. | |
| 4,123,377 | A * | 10/1978 | Davey | C11D 3/3953 252/187.27 |
| 4,155,871 | A * | 5/1979 | Donaldson | C11D 1/83 510/108 |
| 4,236,891 | A * | 12/1980 | Scardera | D06L 3/068 252/187.27 |
| 4,380,533 | A | 4/1983 | Wojtowicz | |
| 4,561,994 | A | 12/1985 | Rubin et al. | |
| 4,961,751 | A * | 10/1990 | Eissele | D06L 3/02 8/101 |
| 6,162,371 | A | 12/2000 | Rees | |
| 6,534,463 | B1 * | 3/2003 | Briatore | C11D 3/042 510/348 |
| 6,566,574 | B1 | 5/2003 | Tadros et al. | |
| 6,998,379 | B1 * | 2/2006 | Costagliola | C11D 3/2075 510/372 |
| 7,255,797 | B2 * | 8/2007 | Martin | A01N 59/02 210/198.1 |
| 7,465,412 | B2 | 12/2008 | Pickens et al. | |

(Continued)

FOREIGN PATENT DOCUMENTS

| | | |
|---|---|---|
| CA | 1190357 | 7/1985 |
| FR | 940754 | 12/1948 |
| GB | 574979 | 1/1946 |

OTHER PUBLICATIONS

Literature: Joseph William Mellor; 'A Comprehensive Treatise on Inorganic and Theoretical Chemistry', vol. II; Longmans, Green and Co.; Fifth Avenue, New York; pp. 250-289; 1922.

(Continued)

*Primary Examiner* — Gregory R Delcotto
(74) *Attorney, Agent, or Firm* — Alok Goel

(57) ABSTRACT

The invention relates to compositions, methods of use, and methods of manufacture for an intercalated bleach compound and compositions thereof. The intercalated bleach compound has the formula $M_x(OCl)_y(O)_m(OH)_n$ where M is an alkaline earth metal such as magnesium, calcium or mixture thereof. The values of x and y independently equal any number greater than or equal to 1 (e.g., 1, 2, 3, 4, etc.), and m and n independently equal any number greater than or equal to 0 (e.g., 0, 1, 2, 3, 4, etc.), but m and n are not both 0. In addition, the molar ratio of the alkaline earth metal (e.g., magnesium or calcium) to hypochlorite is at least 3:1. In other words, x is ≥3y. The compounds exhibit excellent stability, little or no chlorine bleach odor, exhibit excellent pH buffering characteristics, and less reactivity with organic materials as compared to alternative chlorine bleach products.

20 Claims, 11 Drawing Sheets

(56) References Cited

U.S. PATENT DOCUMENTS

| | | | |
|---|---|---|---|
| 8,287,755 B2* | 10/2012 | Smith | C11D 3/349 252/186.37 |
| 8,361,944 B2* | 1/2013 | Smith | C11D 3/10 252/186.37 |
| 8,361,945 B2* | 1/2013 | Smith | A61K 8/466 252/186.37 |
| 9,074,164 B2* | 7/2015 | Rumberger | C11D 3/3953 |
| 9,353,336 B2* | 5/2016 | Rumberger | C11D 3/3953 |
| 2004/0101881 A1* | 5/2004 | Durmowicz | C12Q 1/6848 435/6.13 |
| 2004/0168260 A1 | 9/2004 | Taylor | |
| 2012/0141568 A1 | 6/2012 | Privitera et al. | |
| 2013/0109609 A1 | 5/2013 | Smith et al. | |

OTHER PUBLICATIONS

International Search Report PCT/US13/64163; The Clorox Company; Dec. 2, 2013; 3 pages.
International Search Report PCT/US13/64157; The Clorox Company; Dec. 6, 2013; 3 pages.
USPTO Non-Final Office Action dated Jun. 16, 2016; U.S. Appl. No. 15/151,268, filed May 10, 2015.

* cited by examiner

INTERCALATED BLEACH COMPOSITIONS, RELATED METHODS OF MANUFACTURE AND USE

CROSS-REFERENCE TO RELATED APPLICATIONS

The present application is a continuation of co-pending U.S. patent application Ser. No. 14/724,349, filed on May 28, 2015 which is a continuation of U.S. patent application Ser. No. 14/050,085, filed on Oct. 9, 2013, now U.S. Pat. No. 9,074,164, issued Jul. 7, 2015, the disclosure of each of the above applications is incorporated by reference in its entirety.

BACKGROUND OF THE INVENTION

1. The Field of the Invention

The present invention relates to bleaching compounds and bleaching compositions including such compounds. In addition to such compounds and compositions, the invention relates to methods of making and using such compounds and compositions.

2. Description of Related Art

Sodium hypochlorite is a highly effective cleaning, bleaching and sanitizing agent that is widely used in cleaning and sanitizing various hard and soft surfaces, in laundry care, etc. Various other chlorine bleach products are available, such as other hypochlorites (e.g., calcium hypochlorite, lithium hypochlorite, sodium hypochlorite phosphate adduct, etc.), isocyanuric acids, isocyanuric acid salts, hydantoins (e.g., dichlorohydantoins), chloroamines (e.g., trichloromelamine), and others. Such various chlorine bleach products exhibit various advantages and disadvantages with respect to formulation flexibility, odor (i.e., existing chlorine bleaches exhibit varying degrees of the distinctive "bleach" odor), clarity of solutions formulated with a given bleach product, stability, levels of available chlorine, chlorine yield, moisture sensitivity, and other criteria.

Generally, any given existing bleach product exhibits a mix of good characteristics with respect to some criteria, and poor characteristics with respect to other criteria. For example, a sodium hypochlorite phosphate adduct bleach product provides excellent solution clarity, and relatively good characteristics relative to formula flexibility, odor, and moisture sensitivity; however it is undesirable for many purposes such as laundry detergents because it contains phosphates. While other bleach products exhibit better characteristics with respect to one or more of stability, chlorine availability, formula flexibility, etc.; these products often exhibit poor characteristics with respect to other criteria. In other words, no existing bleach product provides excellent criteria across a wide range of criteria. As such, there exists a continuing need for improved chlorine bleach compositions.

BRIEF SUMMARY OF THE INVENTION

One aspect of the present invention is directed to a method of using a bleach composition to treat a surface or material. The method includes providing a bleach composition comprising a bleach compound having the formula $M_x(OCl)_y(O)_m(OH)_n$ where M is an alkaline earth metal such as magnesium or calcium. The values of x and y may independently be any number greater than or equal to 1 (e.g., 1, 2, 3, 4, etc.), and m and n may independently be any number greater than or equal to 0 (e.g., 0, 1, 2, 3, 4, etc.), but m and n are not both 0. In addition, the molar ratio of the alkaline earth metal (e.g., magnesium or calcium) to hypochlorite is at least 3:1. In other words, x is ≥3y. The method further comprises contacting the bleach composition with a surface or material to treat the surface (e.g., hard or soft) or material (e.g., water, etc.).

Another aspect of the present invention is directed to a method of using a bleach composition to treat a surface or material. The method includes providing a bleach composition comprising a bleach compound having the formula $Mg_x(OCl)_y(O)_m(OH)_n$. The values of x and y may independently be any number greater than or equal to 1 (e.g., 1, 2, 3, 4, etc.), and m and n may independently be any number greater than or equal to 0 (e.g., 0, 1, 2, 3, 4, etc.), but m and n are not both 0. In addition, the molar ratio of the magnesium to hypochlorite is at least 3:1. In other words, x is ≥3y. The method further comprises contacting the bleach composition with a surface or material to treat the surface or material.

Another aspect of the present invention is directed to a method of using a bleach composition to treat a surface or material. The method includes providing a bleach composition comprising a surfactant and a bleach compound having the formula $Mg_x(OCl)_y(O)_m(OH)_n$. The values of x and y may independently be any number greater than or equal to 1 (e.g., 1, 2, 3, 4, etc.), and m and n may independently be any number greater than or equal to 0 (e.g., 0, 1, 2, 3, 4, etc.), but m and n are not both 0. In addition, the molar ratio of the magnesium to hypochlorite is at least 3:1. In other words, x is ≥3y. The method further comprises contacting the bleach composition with a surface or material to treat the surface or material.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Definitions

Figure 1:
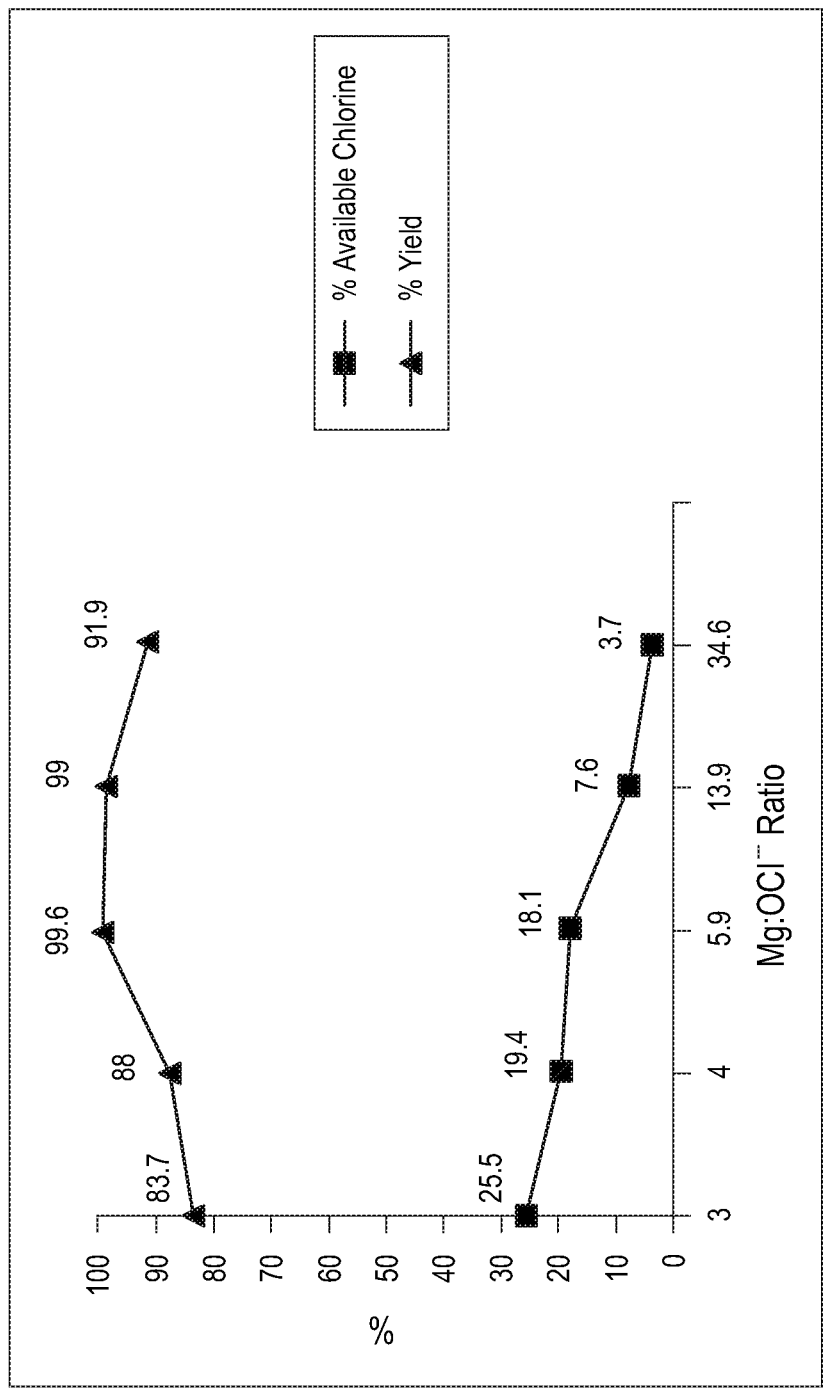
FIG. 1 plots percentage available chlorine and percentage yield data for various magnesium intercalated bleach compositions according to the present invention.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

The term water-soluble polymer as used herein means a polymer which gives an optically clear solution free of precipitates at a concentration of 0.001 grams per 100 grams of water, preferably 0.01 grams/100 grams of water, more preferably 0.1 grams/100 grams of water, and even more preferably 1 gram or more per 100 grams of water, at 25° C.

As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." The term "disinfect" may generally refer to the elimination of many or all pathogenic microorganisms on surfaces with the exception of bacterial endospores. The term "sterilize" may refer to the complete elimination or destruction of all forms of microbial life and which is authorized under the applicable regulatory laws to make legal claims as a "sterilant" or to have sterilizing properties or qualities.

The term "cleaning composition" as used herein, is meant to mean and include a cleaning formulation having at least one surfactant.

The term "laundry composition" as used herein, is meant to mean and include a laundry formulation having at least one surfactant.

The term "surfactant" as used herein, is meant to mean and include a substance or compound that reduces surface tension when dissolved in water or water solutions, or that reduces interfacial tension between two liquids, or between a liquid and a solid. The term "surfactant" thus includes anionic, nonionic, cationic, zwitterionic and/or amphoteric agents.

In the application, effective amounts are generally those amounts listed as the ranges or levels of ingredients in the descriptions, which follow hereto. Unless otherwise stated, amounts listed in percentage ("wt %'s") are in weight percent (based on 100 weight % active) of the particular material present in the referenced composition, any remaining percentage being water or an aqueous carrier sufficient to account for 100% of the composition, or for solid forms any remaining percentage being magnesium or calcium salts unless otherwise noted. For very low weight percentages, the term "ppm" corresponding to parts per million on a weight/weight basis may be used, noting that 1.0 wt % corresponds to 10,000 ppm.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

II. Intercalated Bleach Compositions

The present invention is directed to bleaching compounds and compositions including such bleaching compounds. The bleaching compounds are believed to be intercalated bleach compounds that may include an alkaline earth hypochlorite species intercalated with oxide and/or hydroxide species. The inventors have found that the intercalated bleach compounds exhibit excellent stability (e.g., equal to or better than any other known chlorine bleach species), little or no characteristic chlorine bleach odor as compared to other forms of chlorine bleach, exhibit excellent pH buffering characteristics at significantly gentler pH ranges (e.g., about 8 to about 11.5) than existing liquid bleach compositions (11.5 to 13.5). The intercalated bleach compound is stable, even in high humidity environments, and shows relatively less reactivity with organic materials as compared to other solid chlorine bleach alternatives. The material does not appear to show evidence of any self-propagating decomposition reactions, can be provided in solid form (which can be dissolved or suspended into aqueous solution), and does not readily clump or cake as do many existing alternative chlorine bleaches. The material exhibits better flexibility as to its compatibility with various adjuvants than existing alternatives, can be formulated to control release of hypochlorite over a desired period of time, and may be formulated within compositions that are phosphate free while providing the above benefits.

As used herein, when referring to the inventive compositions, it is meant a composition including the intercalated bleach compound. The composition may optionally include further components, if desired.

The compositions may be employed in a very wide range of environments and uses, such as laundry detergents or additives (e.g., cleaning and sanitizing laundry), hard and soft surface cleaning, disinfecting and sanitizing, dishwashing, toilet bowl cleaning, disinfecting, and sanitizing, water purification, sanitizers, lotions, and soaps for skin disinfection and care (e.g., hand sanitizer), spot cleaning, stain pre-treatments, additives for building materials (e.g., grout, drywall, paint, etc.) for mold and mildew inhibition purposes, etc.

The composition could be applied directly as a solid or scouring hypochlorite-releasing bleach formulation, such as a toilet bowl sanitizer, dry laundry detergent or additive, or hard surface (e.g., floors, walls, countertops, etc.) cleaner. The compositions may also be provided in concentrated water-dilutable forms, such as powders, tablets, or in pouches.

Specific possible uses include, but are not limited to, general cleaning (e.g., hard or soft surface cleaning/disinfection), a solid employed as an odor absorber/destroyer/deodorizer, an additive for animal litter for odor control and antimicrobial benefits, a solid bleach/solid acid mixture that dissolves immediately in water to form a hard surface disinfectant, automatic toilet bowl cleaner, bleaching laundry (e.g., unit dose, a suspension—stable in bottle with additives, which dissolves in lower pH, dilution by wash water, or a solid powder), a mold inhibitor/allergen prevention and destroyer, liquid solution delivered by trigger spray or attenuated dual chamber spray bottle, as an aerosol with an attenuated dual chamber bottle (this is the first possibility of having an aerosol with bleach), skin care/disinfection, building materials (e.g., grout, paint, drywall, etc.), or any application where a solid hypochlorite is desired, but the bleach odor typically associated therewith is not.

Because the intercalated bleach compounds can exhibit little to no chlorine bleach odor, they may be used in formulations where this odor is unwanted, while still delivering the cleaning and micro-efficacy benefits associated with liquid hypochlorite solutions.

The compositions may be used indirectly in bleach-generating systems. For example, a solution may be reconstituted from the solid (e.g., powder) either directly, or by means of a flow through system where liquid (e.g., water) is passed over or in contact with the solid. The resulting solution may optionally be filtered.

Hypochlorite release from the intercalated bleach containing compositions can be controlled through formulation with acids or other compounds that may aid in the solubility of magnesium and/or calcium salts. For example, without such additives, a magnesium intercalated bleach compound may be relatively insoluble, releasing ppm levels of hypochlorite slowly and approximately linearly over time. With the inclusion of selected additives (e.g., a solid acid), hypochlorite release can be made to be substantially instantaneous, upon contact with water. In addition, intercalated bleach compositions in solid form including the solid intercalated bleach and a solid acid (e.g., potassium bisulfate, boric acid, succinic acid, etc.) exhibit excellent stability, without initiation of any acid/base reaction prior to contacting the solid with water.

The intercalated bleach compounds can be formulated with a wide variety of adjuvants. For example, the compositions may include a wide range of surfactants, acids, chelating agents, fragrances, alcohols, polymers, etc. that are beneficial in cleaning formulations, even where such adjuvants are organic, including various organic functional groups. In other words, the intercalated bleach compounds are significantly less reactive with organic compounds than other hypochlorite bleach alternatives.

The compositions may be adhered to a cleaning wipe substrate to make a dry hypochlorite-releasing wipe. In the case of magnesium intercalated bleach, the magnesium oxide will likely still have some positive charge character, enhancing cleaning performance, allergen cleaning, and micro-efficacy of the wipe where negatively charged species may be present. Such embodiments would also be expected to exhibit increased stability as compared to current bleach wipe products, due to the stability characteristics of the intercalated bleach compounds as compared to existing alternatives.

The composition may be in solid form, e.g., in the form of a powder, tablet, or granule. These forms may be used in any application where a solid hypochlorite-releasing bleach is desired. Aqueous or other liquid solutions may be prepared therefrom.

Methods of using the composition are also disclosed herein. Methods of using the composition generally include contacting the composition with a surface (e.g., countertop, floor, laundry) or material (e.g., toilet bowl water) such that the composition treats (e.g., cleans, sanitizes and/or disinfects) the surface or material.

Methods of making the intercalated bleach compounds and compositions are also disclosed herein. The intercalated bleach compositions are generally the product of reaction of an aqueous solution of alkaline earth metal (e.g., calcium) or alkali metal (e.g., sodium) hypochlorite solution mixed with an alkaline earth metal (e.g., magnesium or calcium) salt such as magnesium oxide. For example, a magnesium intercalated bleach compound may be obtained from the product of evaporation of an aqueous solution of calcium or sodium hypochlorite solution mixed with magnesium oxide. The intercalated bleach compound has a molar ratio of alkaline earth metal (e.g., magnesium or calcium) to hypochlorite that is greater than or equal to 3. A calcium intercalated bleach compound could be similarly formed by mixing the hypochlorite solution with calcium oxide, rather than magnesium oxide.

In an embodiment, the available chlorine concentration may be from about 0.01% to about 25%, or from about 0.1% to about 25% %, or from about 1% to about 25%, or from about 2.5% to 25%.

The intercalated bleach compound is believed to generally have the formula $M_x(OCl)_y(O)_m(OH)_n$:

wherein M is an alkaline earth metal or mixture of alkaline earth metals, such as magnesium or calcium or mixtures thereof;

wherein x and y independently equal any number greater than or equal to 1 (e.g., 1, 2, 3, 4, etc.);

wherein m and n independently equal 0 or any number greater than 0 (e.g., 0, 1, 2, 3, 4, etc.), but m and n are not both 0; and wherein x is $\geq 3y$.

The values of x, y, m, and n may be integers (i.e., whole numbers). By way of further example, in an embodiment, $2m+n \geq 5y$. In another embodiment, $x=0.5y+m+0.5n$.

One or more adjuvants may be included in the composition. For example, such adjuvants may include, but are not limited to surfactants, acids, builders, water-soluble polymers, and cross-linked water-swellable polymers.

A. Builders

The composition can contain a builder. In an embodiment, the builder may be present in an amount ranging from about 1% to about 90%, about 50% to about 80%, about 10% to about 60%, or about 25% to about 50%. The builder can be selected from inorganic builders (e.g., sulfates, carbonates, bicarbonates, sesquicarbonates, clays, zeolites, silicates, aluminas, aluminasilicates, and mixtures thereof), such as alkali metal carbonate, alkali metal bicarbonate, alkali metal hydroxide, alkali metal silicate, alkali metal halide and combinations thereof.

A builder may increase the effectiveness of an included surfactant, can function as a softener, a sequestering or chelating agent, a buffering agent, a diluent or filler, a carrier or a pH adjusting agent in the composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxy-sulfonates, sucrose starch derivatives, cellulose gum, bitumen, clay, corn starch, cellulose gum, FeAl aluminide intermetallic, Fuller's earth, lignosulfonate, hydrated lime, molasses, finely ground waste paper, water, wax, polyacrylic acid and polyacrylates, other polymers (polyethyleneimine and polyacrylamide), liquid polybutadine emulsion, adhesives, tar, pitch and mixtures thereof.

Builders, when used, include, but are not limited to, organic acids, mineral acids, alkali metal and alkaline earth salts of silicate, metasilicate, polysilicate, aluminosilicate, borate, borax, sulfates, hydroxide, carbonate, bicarbonate, sesquicarbonate, carbamate, phosphate, polyphosphate, pyrophosphates, triphosphates, tetraphosphates, ammonia, hydroxide, monoethanolamine, monopropanolamine, diethanolamine, dipropanol-amine, triethanolamine, and 2-amino-2methylpropanol. Other suitable buffers include ammonium carbamate, citric acid, formic acid, formate salts and acetic acid.

Additional details of builders and buffers can be found in WO 95/07971, which is incorporated herein by reference. The term silicate is meant to encompass silicate, metasilicate, polysilicate, aluminosilicate and similar compounds. More specific examples include sodium tetraborate, sodium carbonate, sodium bicarbonate, sodium sesquicarbonate, potassium carbonate, potassium bicarbonate, sodium and potassium zeolites. Exemplary organic non-phosphate builders and sequestrant salts include alkali metal salts of polycarboxylic acids and nitriloacetic acid. More specific examples include monosodium, disodium and trisodium citrate, and tetrasodium ethylenediaminetetraacetate (EDTA-Na$_4$), diethylene triamine pentaacetic acid (DTPA), dipropylethyl tetraamine, ethylene diamine disuccinic salt, ethylenediamine (EDA) and derivatives, diethylenetriamine (DETA), aminoethylethanolamine (AEEA). Salts and derivatives of organic acids (e.g., citric acid and tartaric acid, glutamic acid, formic acid, succinic acid), and amino acid based components may also be suitable for use.

B. Polymers

The composition can contain a water-soluble polymer. Examples of water-soluble polymer include, but are not limited to, polycarboxylate, sulfonated carboxylate, polysulfonate, polyvinylpyrrolidone ("PVP"), polyacrylic acid, polyacrylate, copolymers and mixtures thereof, and mixtures thereof.

Examples of polycarboxylate include, but are not limited to, polymers with sufficient carboxylate ions to achieve water solubility. Carboxylate ions may be derived from various monomers including acrylic acid, maleic acid and maleic anhydride. Copolymers of different carboxylate-containing monomers are also suitable as well as copolymers with non-carboxylate containing monomers such as methacrylate, acrylonitrile, styrene, ethylene, propylene, and many others. Mixtures of carboxylate containing polymers can also be used.

In an embodiment, the molecular weight of the water-soluble polymer may be between about 1,000 to about 100,000 Daltons, about 2,000 to about 80,000 Daltons, about 3,000 to about 10,000 Daltons, or about 3,000 to about 5,000 Daltons. The water-soluble polymer may be present in an amount ranging from about 0.1% to about 60%, about 5% to about 50%, about 10% to about 40%, or about 20% to about 30%.

The composition may contain a cross-linked water-swellable polymer. Examples of water-swellable polymer include, but are not limited to, cross-linked polycarboxylate, cross-linked polysulfonate, cross-linked carboxymethylcellulose, cross-linked PVP, cellulose, sodium carboxymethylcellulose and mixtures thereof.

In an embodiment, the molecular weight of the water-swellable polymer may be between about 1,000 to about 100,000 Daltons, about 2,000 to about 80,000 Daltons, or about 3,000 to about 10,000 Daltons or about 3,000 Daltons to about 5,000 Daltons. The water-swellable polymer may be present in an amount ranging from about 0.1% to about 60%, about 5% to about 50%, about 10% to about 40%, or about 20% to about 30%.

Polymers may also include both high and low molecular weight polymers and any monomers or oligomers, waxes, polymeric surfactants, latex, silicones, silicone polyether, copolymers, maleic/acrylic copolymers, dimethicone, hydrogenated castor oil, saccharides, and any weight polyethylene glycol. In addition, the category of polymers could include but is not limited to polyethyleneimine ethoxylate propoxylate, diquaternium ethoxysulfate, polyethyleneimine ethoxylate, glycerine, PEG-136 polyvinylacetate, polyacrylamide quaternium chloride.

C. Acids

The composition may contain an acid. Inclusion of an acid (e.g., a solid acid) may aid in controlling the release profile of hypochlorite from the intercalated bleach compound. Examples of acids that can be used with the present invention may include, but are not limited to, sulfonic acid, sulfamic acid, boric acid, siliceous acids, hydrochloric acid, sulfuric acid, phosphoric acid, dicarboxylic acid, monocarboxylic acid, aminocarboxylic acid, 2-hydroxy-1,2,3-propanetricarboxylic acid, organic acids such as but not limited to citric acid, adipic acid, succinic acid, acrylic acid, polyacrylic acid, lauric acid, lactic acid, acetic acid, hydroxyacetic acid, acid salts, and mixtures thereof. Specific examples of acids, include but are not limited to, succinic acid, glutaric acid, 3-pyridine sulfonic acid, dodecyl benzene sulfonic acid, and mixtures thereof. In an embodiment, an included acid may be in solid form. Examples of such solid acids include inorganic acidic salts such as potassium bisulfate, magnesium chloride or other acidic metal salts, hydrogen phosphate salts, sodium bicarbonate, organic acids such as succinic acid, fatty acids, nucleic acids palmitic acid, and Lewis acids such as boric acid. Acidic gases or nonmetal oxides may also be included, for example carbon dioxide. Any acids may be present in an amount ranging from about 0.1% to about 75%, about 5% to about 50%, about 10% to about 40%, or about 20% to about 30%.

D. Bases

The composition may contain one or more bases selected from inorganic, organic, and amphoteric bases and mixtures thereof. Inclusion of a base (e.g., a solid base) may aid in controlling the release profile of hypochlorite from the intercalated bleach compound. Examples of bases that can be used with the present invention may include, but are not limited to, any hydroxide salt, metal oxides, amphoteric oxides, carbonates, phosphates, borate, citrate, acetate, formate and any mixtures or salts thereof. Any bases may be present in an amount ranging from about 0.1% to about 75%, about 5% to about 50%, about 10% to about 40%, or about 20% to about 30%.

E. Surfactants

The composition may contain one or more surfactants selected from nonionic, anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. The surfactants may be present at a level of from about 0.1% to about 75%, from about 5% to about 50%, or from about 10% to about 30%.

The composition may comprise an anionic surfactant. Exemplary anionic surfactants may include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, alkyl disulfates, alcohol sulfates, sodium palmitate, or as salts of fatty acids as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl) glucamine sulfates, and sulfates of alkylpolysacchanides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates, which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. Mixtures of alkyl sulfate and/or sulfonate and alkyl ethoxysulfate surfactants may be employed. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps ("alkyl carboxyls"), especially certain secondary soaps as described herein. Suitable alkyl ethoxy carboxylates include those with the formula $$RO(CH_2CH_2O)_xCH_2COO^-M^+$$

wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula RO—(CHR$^1$—CHR$^2$—O)—R$^3$ wherein R is a C6 to C18 alkyl group, x is from 1 to 25, R$^1$ and R$^2$ are selected from the group consisting of hydrogen, methyl acid radical, succinic acid radical, hydroxysuccinic acid radical, and mixtures thereof, and R$^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula R—CON(R$^1$)CH—)COOM, wherein R is a C5-C17 linear or branched alkyl or alkenyl group, R$^1$ is a C1-C4 alkyl group and M is an alkali metal ion. Examples are the myristyl and oleoyl methyl sarcosinates in the form of their sodium salts.

Other suitable surfactants include fatty acid sarosinates which are mild, biodegradable anionic surfactants derived from fatty acids and sarcosine (amino acid). Sarcosine is the N-methyl derivative of glycine. Sarcosine is a natural amino acid found in muscles and other tissues. Sarcosine is found naturally as an intermediate in the metabolism of choline to glycine. In a preferred embodiment, the sarcosines are acyl sarcosines. Examples of acyl sarcosines include, but are not limited to, cocoyl sarcosine, lauroyl sarcosine, myristoyl sarcosine, oleoyl sarcosine, stearoyl sarcosine which are modified fatty acids. The salts of acyl sarcosines are referred to acyl sarcosinates. Acyl sarcosinates useful herein include, for example, those having a formula:

$$RCON(CH_3)CH2COOX$$

wherein R is an alkyl or alkenyl having from 8 to 22 carbon atoms, preferably from 12 to 18 carbon atoms, more preferably from 12 to 14 carbon atoms; and X is a sodium, potassium, ammonium, or triethanolamine.

Examples of acyl sarcosinates that can be used with the present invention include, but not limited to, sodium coccyl sarcosinate, sodium lauroyl sarcosinate and sodium myristoyl sarcosinate, sodium oleoyl sarcosinate, sodium stearoyl sarcosinate, ammonium coccyl sarcosinate, ammonium lauroyl sarcosinate and ammonium myristoyl sarcosinate, ammonium oleoyl sarcosinate and ammonium stearoyl sarcosinate. Commercially available preferred acyl sarcosinates include, but are not limited to, for example, sodium lauroyl sarcosinate having the tradename Hamposyl® L30 which is available from Hampshire Chemicals, and sodium cocoyl sarcosinate having the tradename Hamposyl® C30 which is available from Hampshire Chemicals.

Other suitable surfactants may include fatty alcohol sulfate which has a higher alcohol or alkyl group is normally in the range of 10 to 18 carbon atoms. The cation will almost invariably be sodium or will include sodium, although other cations, such as triethanolamine, potassium, ammonium, magnesium and calcium may also be employed. Exemplary fatty alcohol sulfates may include those wherein the fatty alcohol is essentially saturated and is of carbon content(s) within the 10 to 18 carbon atoms range, preferably 10 or 12 to 14 or 16 carbon atoms, such as 12 to 16, or that is derived from coconut oil (coco), palm oil, or palm kernel oil. Lauryl sulfates, and particularly, sodium lauryl sulfate, may be preferred primary detergents but such designation also may apply to such detergents wherein the carbon chain length of the alcohol is not limited to 12 carbon atoms, but is primarily (over 50% and normally over 70 or 75%) of 12 to 14 carbon atoms. Such materials may be obtained from natural sources, such as coconut oil and palm kernel oil. In one embodiment, the fatty alcohol sulfate is a C12-C18 fatty alcohol sulfate. In another embodiment, the fatty alcohol sulfate is a C12-C16 fatty alcohol sulfate. In another embodiment, the fatty alcohol sulfate is a C12-C14 fatty alcohol sulfate. In another embodiment, the fatty alcohol is a C12 fatty alcohol sulfate. In another embodiment, the fatty alcohol sulfate is sodium lauryl sulfate. In a specific embodiment, the fatty alcohol sulfate is a sodium coco fatty alcohol sulfate.

Suitable amphoteric surfactants for use herein may include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants may be exemplary zwittenionic surfactants for use herein.

Suitable betaines are those compounds having the formula $R(R^1)_2N^+R^2COO^-$ wherein R is a C6-C18 hydrocarbyl group, each $R^1$ is typically C1-C3 alkyl, and $R^2$ is a C1-C5 hydrocarbyl group. Suitable betaines are C12-18 dimethylammonio hexanoate and the C10-18 acylamidopropane (or ethane) dimethyl (or diethyl) betaines. Complex betaine surfactants are also suitable for use herein.

Suitable cationic surfactants to be used herein may include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants. Additional suitable cationic surfactants include coco fatty acid diethanolamine, hydrogenated palm tea ester quat, and cationic ethyoxylate fatty acids.

Another group of cationic surfactants that may be suitable for use is cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting, of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example —CH$_2$—O—, CH$_2$— and —CH$_2$—NH—CH$_2$— linkages are included. The spacer group chain may comprise only carbon atoms, or the chain is a hydrocarbyl chain.

The composition may comprise cationic mono-alkoxylated amine surfactants, for instance, of the general formula: $R^1R^2R^3N^+ApR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $ApR^4$ groups are —CH$_2$CH$_2$—OH, —CH$_2$CH$_2$CH$_2$—OH, —CH$_2$CH(CH$_3$)—OH and —CH(CH$_3$)CH$_2$—OH. Suitable $R^1$ groups are linear alkyl groups, for instance, linear $R^1$ groups having from 8 to 14 carbon atoms.

Suitable cationic mono-alkoxylated amine surfactants for use herein may be of the formula $R^1(CH_3)(CH_3)N^+(CH_2CH_2O)_{2-5}H\ X^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy (CH$_2$CH$_2$O) units (EO) are replaced by butoxy, isopropoxy [CH(CH$_3$)CH$_2$O] and [CH$_2$CH(CH$_3$)O] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality. A and A' can vary independently and are each selected from C1-C4 alkoxy, for instance, ethoxy, (i.e., —$CH_2CH_2O$—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein may be of the formula $R^1CH_3N^+(CH_2CH_2OH)(CH_2CH_2OH)$ $X^-$, wherein $R^1$ is C10-C18 hydrocarbyl and mixtures thereof, or C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+$—$(CH_2CH_2O)_pH$—$(CH_2CH_2O)_qH$ $X^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethylene ethanols.

An example of a suitable cationic fluorosurfactant compound may have the following structure: $C_nF_{2n+1}SO_2NHC_3H_6N^+(CH_3)_3I^+$ where n~8. This cationic fluorosurfactant is available under the tradename Fluorad® FC-135 from 3M. Another example of a suitable cationic fluorosurfactant is $F_3$

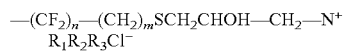
—$(CF_2)_n$—$(CH_2)_m$$SCH_2CHOH$—$CH_2$—$N^+$
$R_1R_2R_3Cl^-$ wherein: n is 5-9 and m is 2, and $R_1$, $R_2$ and $R_3$ are —$CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants that may be suitable for use in the present invention are also described in EP 866,115 to Leach and Niwata. The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

The composition may comprise a nonionic surfactant. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, may be suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein may include those having the structural formula $R^2CONR^1Z$ wherein: $R^1$ is H, C1-C4 hydrocarbyl, 2-hydroxyethyl, 2-hydroxypropyl, ethoxy, propoxy, or a mixture thereof, for instance, C1-C4 alkyl, or C1 or C2 alkyl; and $R^2$ is a C5-C31 hydrocarbyl, for instance, straight-chain C5-C19 alkyl or alkenyl, or straight-chain C9-C17 alkyl or alkenyl, or straight-chain C11-C17 alkyl or alkenyl, or mixture thereof, and Z is a polyhydroxyhydrocarbyl having a linear hydrocarbyl chain with at least 3 hydroxyls directly connected to the chain, or an alkoxylated derivative (for example, ethoxylated or propoxylated) thereof. Z may be derived from a reducing sugar in a reductive amination reaction, for example, Z is a glycityl.

Suitable fatty acid amide surfactants may include those having the formula: $R^1CON(R^2)_2$ wherein $R^1$ is an alkyl group containing from 7 to 21, or from 9 to 17 carbon atoms and each $R^2$ is selected from the group consisting of hydrogen, C1-C4 alkyl, C1-C4 hydroxyalkyl, and —$(C_2H_4O)_xH$, where x is in the range of from 1 to 3.

Alkylpolysaccharides that may be suitable for use herein are disclosed in U.S. Pat. No. 4,565,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Other suitable nonionic surfactants may include food safe nonionic surfactants. Examples of food safe nonionic surfactants are sucrose esters, such as sucrose cocoate available from Croda, and sorbitan esters, such as polyoxyethylene (20) sorbitan monooleate from J.T. Baker and polyoxyethylene(20) sorbitan monolaurate from Uniquema. Other examples of food safe nonionic surfactants are given in Generally Recognized As Safe (GRAS) lists, as described below.

In an embodiment, the compositions may specifically contain alkyl polyglucoside ("APG") surfactant. Suitable alkyl polyglucoside surfactants may include alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al., which are all incorporated by reference. Suitable alkyl polyglucosides for use herein may also be disclosed in U.S. Pat. No. 4,565,647 to Lienado, describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide may be ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula: $R^2O(C_nH_{2n}O)_t(glucosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl may be derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

A group of alkyl glycoside surfactants suitable for use in the practice of this invention may be represented by formula I below:

wherein R is a monovalent organic radical containing from about 6 to about 30 (preferably from about 8 to about 18) carbon atoms; $R^2$ is a divalent hydrocarbon radical containing from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, $-CH_2OH$, is oxidized to form a $-CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglyco-side available from Dow Chemical Company), AG6202® (a $C_8$ alkyl polyglycoside available from Akzo Nobel) Glucopon® 425N (a $C_8$-$C_{16}$ alkyl polyglycoside available from Cognis Corporation), Glucopon® 215 (a $C_8$-$C_{10}$ alkyl polyglycoside available from Cognis Corporation), Glucpon® 225 (a $C_8$-$C_{10}$ alkyl polyglycoside available from Cognis Corporation) and Alkadet 15® (a $C_8$-$C_{10}$ alkyl polyglycoside available from Huntsman Corporation). A C8 to C10 alkylpolyglucoside includes alkylpoly-glucosides wherein the alkyl group is substantially C8 alkyl, substantially C10 alkyl, or a mixture of substantially C8 and C10 alkyl. Additionally, short chain APGs such as C4 and/or C6 or mixtures thereof may be suitable with the present invention.

E. Additional Adjuvants

Exemplary specific chelating agent sequestrants and/or optical brightener components that may be used include, but are not limited to, sodium polyacrylate (e.g., ACCUSOL™ 445N), $Na_3$ methyl glycine diacetate (e.g., TRILON® M LIQUID), $Na_4$ glutamic acid diacetate (DISSOLVINE® GL47S), hybrid biopolymers (e.g., ALCOGUARD® HS5240), sodium polyitaconate (e.g., ITACONIX™ DSP2K-US), $Na_x$ carboxymethyl inulin (COSUN CMI 25-40D or DEQUEST® SPE 15625), TINOSORB FB, triazine-stilbenes including di-, tetra-, or hex-sulfonated derivatives, coumarins, imidazolines, diazoles, triazoles, benzoxazolines, biphenyl-stilbenes and combinations thereof.

Various polyacrylates are of course suitable for use. Examples of such sequestrants are disclosed in U.S. Pat. Nos. 6,211,131 and 6,297,209, each of which is herein incorporated by reference in its entirety.

The composition may include one or more preservatives. When used, such adjuvants may include, but are not limited to, methyl, ethyl and propyl parabens, phosphates such as trisodium phosphate, short chain organic acids (e.g. acetic, lactic and/or glycolic acids), bisguanidine compounds (e.g. DANTAGARD and/or GLYDANT) and/or short chain alcohols (e.g. ethanol and/or IPA). Additional details of exemplary preservatives are disclosed in U.S. Publication 2013/0028990, incorporated herein by reference.

Solvents other than water may also be employed (e.g., ethanol, isopropanol, glycol ethers, etc.).

Surfactants, silicates, builders, sequestrants, chelating agents, preservatives, fluorescent whitening agents, optical brighteners, fragrances, dyes, pigments, fillers, diluents, desiccants, buffers, solid processing aids, preservatives, colorants, anti-corrosion inhibitors, fragrances, anti-deposition agents, hydrotropes, polymer dispersants (e.g., alcohol ethoxylates), deflocculants, plasticizers, superplasticizers, emulsifiers, detergents, other disinfectants or antimicrobials (e.g., quaternary ammonium compounds, essential oils, metal salts, silver, zinc, enzymes, etc.), enzymes including but not limited to protease, mannanase, cellulose, amylase, pectinase, xyloglucanase, natalase, termamyl, subtilisin, lactase, and any other adjuvants may be included in appropriate, effective amounts. In some embodiments, such levels may be from about 0% to about 90%, or from about 0.001% to about 50%, or from about 0.01% to about 25% by weight. Alternatively, any given adjuvant or class of adjuvants may be present at a level of from about 0.1 to about 10% by weight, or from about 0.1 to about 5% by weight, or from about 0.1 to about 1% by weight.

Additional details of various adjuvants, their concentration amounts, and other details can be found in U.S. Pat. No. 8,287,755, herein incorporated by reference.

III. Examples and Testing Results

As described above, the intercalated bleach compounds can be formed by evaporating water from an aqueous solution of calcium or sodium hypochlorite solution mixed with magnesium salts such as magnesium oxide. The intercalated bleach compounds have a molar ratio of alkaline earth metal to hypochlorite of greater than or equal to 3.

Various other alkali metal and alkaline earth metal salts may be included with the intercalated bleach compound in the intercalated bleach composition. For example, alkaline earth oxides, alkaline earth hydroxides, alkaline earth carbonates, alkaline earth bicarbonates, alkaline earth chlorides, alkali chlorides, alkali carbonates, alkali bicarbonates, and combinations thereof may be mixed therewith. Specific examples of such salts include, but are not limited to magnesium oxide, magnesium oxide adduct, magnesium hydroxide, magnesium hydroxide adduct, magnesium chloride trihydroxide, magnesium chloride pentahydroxide, magnesium carbonate, magnesium chloride, calcium oxide, calcium hydroxide, calcium carbonate, calcium chloride, sodium chloride, sodium carbonate, sodium bicarbonate, and combinations thereof. Hydrates of such salts may also be included.

Magnesium oxide is a water insoluble, high isoelectric, inorganic material. The high isoelectric point of magnesium oxide (e.g., about 12-13) results in a solution/surface interface that is typically positively charged. The isoelectric point of a material is the pH at which the particular material carries no net electrical charge. Because the solution/surface interface is thus typically positively charged, the magnesium oxide has an affinity for interaction with anionic species. It is believed that the positively charged magnesium oxide surface absorbs negatively charged hypochlorite anions. Further reaction and intercalation of the hypochlorite anions with the magnesium oxide yields a previously unrecognized hypochlorite releasing material. This intercalated bleach compound is substantially different from the starting materials, as evidenced by x-ray diffraction, yield of releasable hypochlorite, storage stability, solubility, and other characteristics.

Within the compositions prepared, the resulting product is a dry white powder, which is essentially odorless. When added to water, it results in a white suspension resembling milk of magnesia, with concurrent release of hypochlorite and a pH buffering range of about 8 to about 11.5. The powder x-ray diffraction indicates a layered or intercalated material. Available chlorine can be tuned to values as low as about 0.01% up to about 25%. More typical available chlorine values may be from about 1% to about 25% or from about 2.5% to about 25%. The product composition may be a mixture of hydrated salts including, but not limited to a magnesium hypochlorite adduct with a secondary magnesium salt, magnesium hydroxide, magnesium oxide, calcium carbonate, and/or adducts of one or more of the foregoing. The intercalated bleach compound itself may be a hydrate. Such a hypochlorite releasing solid can be used in any application where a solid hypochlorite is desired.

The buffering characteristics provided by the intercalated bleach compound are at pH values (e.g., about 8 to about 11.5) generally more gentle than those typically associated with hypochlorite bleach compositions, while providing excellent stability to the hypochlorite species.

Advantageously, the method of manufacture does not use or produce any chlorine gas. Rather, the materials employed are readily available, economically priced, inorganic natural minerals. The intercalated bleach compound itself may be considered to be derived from natural materials, not requiring use of any petrochemicals. Magnesium oxide is listed as having no limits in tolerance exemptions for active and inert ingredients for use in antimicrobial formulations (e.g., food contact surface sanitizing solutions) as detailed in 40 CFR 180-940. This may expand the potential disinfectant product applications that the intercalated bleach compound may be applied to, as compared to existing hypochlorite releasing products.

Various formulations of magnesium intercalated bleach were formed by providing sodium hypochlorite solution or dissolving calcium hypochlorite solid (or lithium hypochlorite, or potassium hypochlorite solid) into water to make a solution including from about 10% to about 18% of the alkali metal hypochlorite or alkaline earth metal hypochlorite. More generally, such a solution may include from about 3% to about 50%, or about 5% to about 25% of the hypochlorite salt. Where a mixture of hypochlorite salts are included in the aqueous hypochlorite solution, the concentration ranges above may refer to the combined concentration of hypochlorite salts. Where employed, calcium hypochlorite can be mixed with water to solubilize the calcium hypochlorite and give the appropriate weight percent solution. Freshly made calcium hypochlorite solution (e.g., as an intermediate from chlorination of lime) may be used in place of solid calcium hypochlorite, and may be used as is, without addition of additional water, provided the concentration is within a desired range. The hypochlorite solution may also be prepared by any process known in the literature.

Where a hypochlorite is mixed with water, the reaction mixture may be stirred or otherwise mixed for an appropriate period of time (e.g., about 2 to about 5 minutes). More generally, mixing may be from about 0.5 minute to about 1 hour, or about 1 minute to about 10 minutes. Once the aqueous hypochlorite solution is provided, a magnesium or calcium salt may be added thereto, in portions, while stirring (e.g., shear mixing) over an appropriate period of time (e.g., about 2 to about 10 minutes, more generally 0.5 minute to about 1 hour or from 1 minute to about 30 minutes). Once all the magnesium or calcium salt (e.g., magnesium oxide) has been added, the reaction mixture may be mixed for an additional period of time of about 5 minutes to about 10 minutes, or more generally from about 1 minute to about 24 hours, or about 2 minutes to about 6 hours or from about 5 minutes to 1 hour.

The reaction mixture may then be dried by pouring into an appropriate container (e.g., a baking dish) and dried. The inventor formed intercalated bleach compound solids were dried for 16 to 72 hours at temperatures ranging from about 20° C. to about 80° C. More generally, drying time may be from about 1 hour to about 10 days, or from about 8 hours to about 5 days. More generally, drying temperatures may range from ambient temperature (e.g., about 20° C.) to about 200° C., or from ambient temperature to about 150° C. Temperatures above ambient temperature may be achieved by drying in an oven. Once dried, the solid can be broken up and powdered. Solid product may also be pressed or cast into a tablet, puck, or granule form. Of course, dried solid could also be used as is, without powdering granulating, or similar.

As will be appreciated, mixing or stirring mechanisms may be varied (e.g., with or without shear mixing), as may time of reaction, amount of water, concentration of hypochlorite solution, the ratio of hypochlorite salt to magnesium/calcium salt, exclusion or addition of carbon dioxide, drying methods (e.g., spray drying may be employed), and powdering method.

FIG. 1 plots available chlorine versus Mg to OCl ratios for several magnesium intercalated bleach compositions that were actually formed. Percentage yield versus Mg to OCl ratios are also plotted in FIG. 1. For example, as shown in FIG. 1, an intercalated bleach composition having a Mg to OCl ratio of 3:1 had an available chlorine level of 25.5% and a yield of 83.7%. An intercalated bleach composition having a Mg to OCl ratio of 4:1 had an available chlorine level of 19.4% and a yield of 88%. An intercalated bleach composition having a Mg to OCl ratio of 5.9:1 had an available chlorine level of 18.1% and a yield of 99.6%. An intercalated bleach composition having a Mg to OCl ratio of 13.9:1 had an available chlorine level of 7.6% and a yield of 99%. An intercalated bleach composition having a Mg to OCl ratio of 34.6:1 had an available chlorine level of 3.7% and a yield of 91.9%.

As is apparent from FIG. 1, in an embodiment, as the Mg to OCl ratio increases, the level of available chlorine generally decreases, while the percentage yield may generally increase.

Figure 2A:
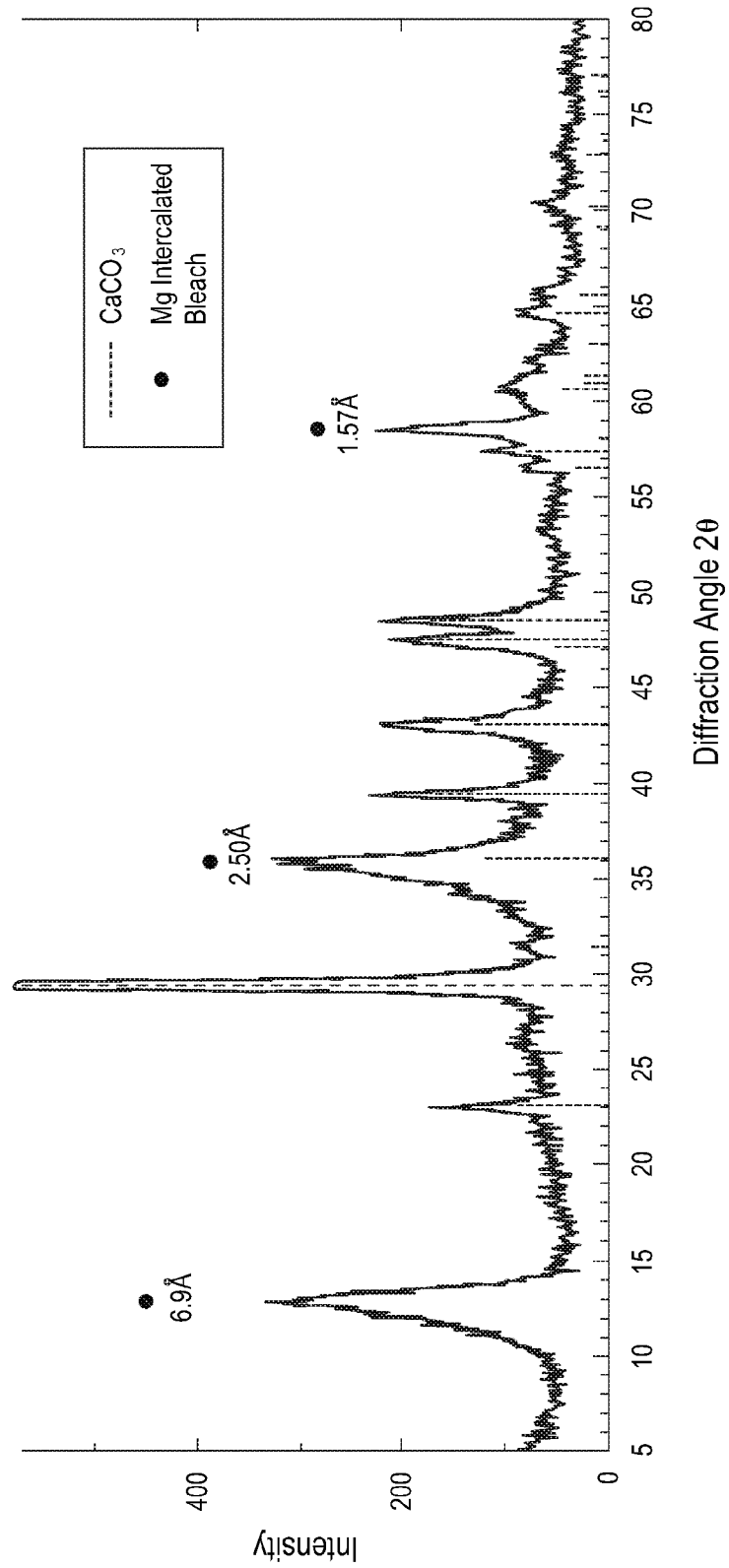
FIG. 2A plots X-ray diffraction ("XRD") spectroscopy data for an exemplary magnesium intercalated bleach composition.
Figure 2B:
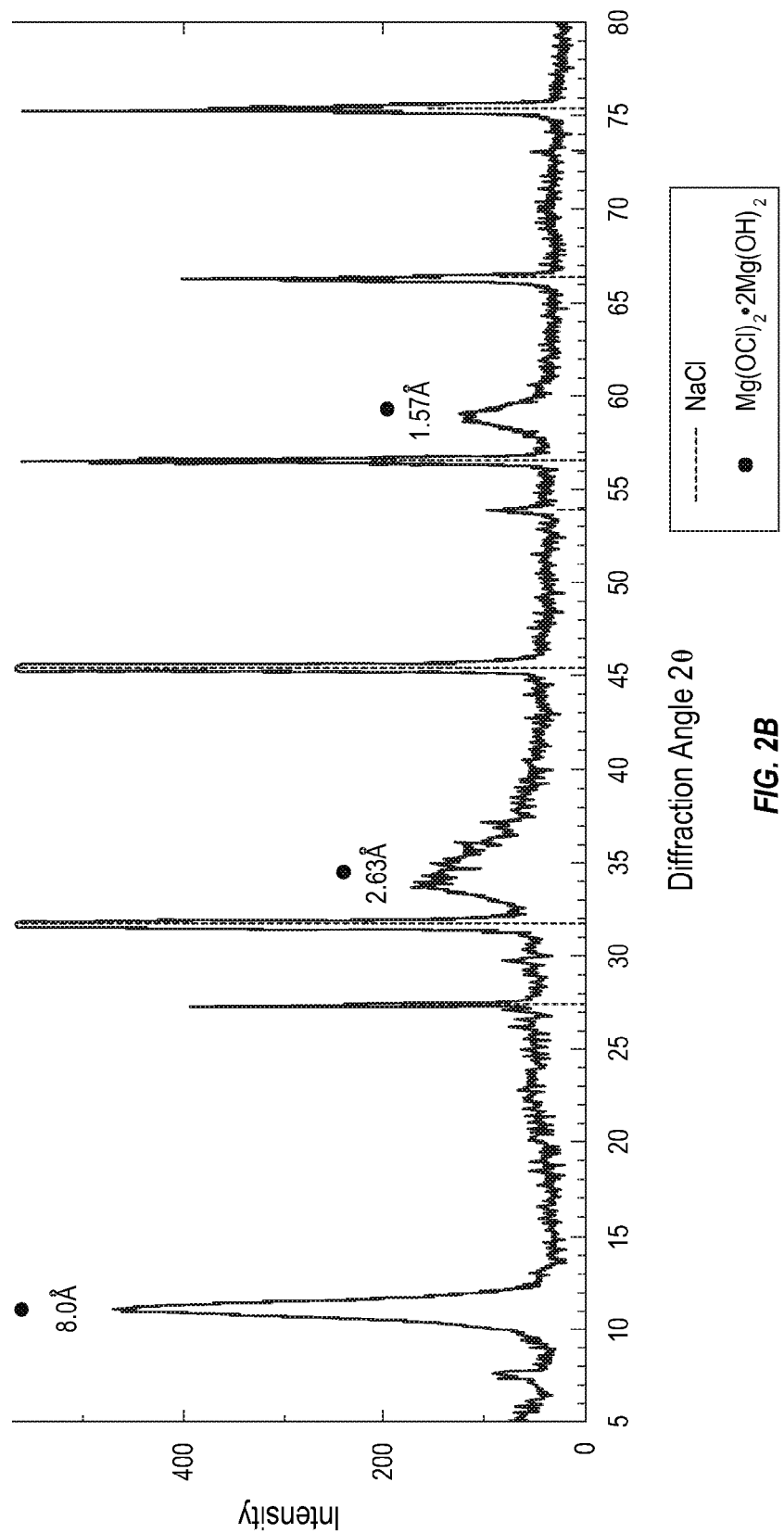
FIG. 2B plots comparative XRD spectroscopy data for a dibasic magnesium hypochlorite bleach composition.

FIG. 2A shows x-ray diffraction ("XRD") angle data for an exemplary magnesium intercalated bleach composition formed as described above. FIG. 2B shows comparative XRD data for dibasic magnesium hypochlorite (Mg(OCl)$_2$·2Mg(OH)$_2$). The data clearly show that the intercalated bleach composition has a XRD response that differs from that of dibasic magnesium hypochlorite. The peak at 6.9 Å is indicative of a layered, intercalated structure (as is the 8.0 Å peak of the dibasic magnesium hypochlorite, which is known to have a layered structure as well).

Mixtures of magnesium intercalated bleach ("MIB") with 7.7% available chlorine and solid form acids (e.g., potassium bisulfate, succinic acid, boric acid, etc.) were observed to exhibit complete stability (with no bleach loss) over a period of 6 weeks at ambient temperature. In other words, no significant acid-base reaction occurred, where the components were present in solid form, where water was substantially absent.

The shelf stability of exemplary magnesium intercalated bleach ("MIB") was evaluated for compositions with and without a sodium lauryl sulfate ("SLS") surfactant. Samples were tested by titration to determine the amount of hypochlorite remaining as compared to an initial amount. From this measured difference, a shelf life was calculated, as shown in Table 1 below.

TABLE 1

| Sample | Initial Titration (wt % OCl) | Final Titration (wt % OCl) | Difference | Sample Age |
|---|---|---|---|---|
| MIB | 7.14 | 7.07 | 0.07 | 1.7 years |
| MIB + SLS | 7.55 | 7.21 | 0.34 | 3 years |

Such extended shelf life stability characteristics (e.g., well over 1 year, greater than 2 years, etc.) are among the best known among chlorine bleach products.

Figures 3A, 3B:
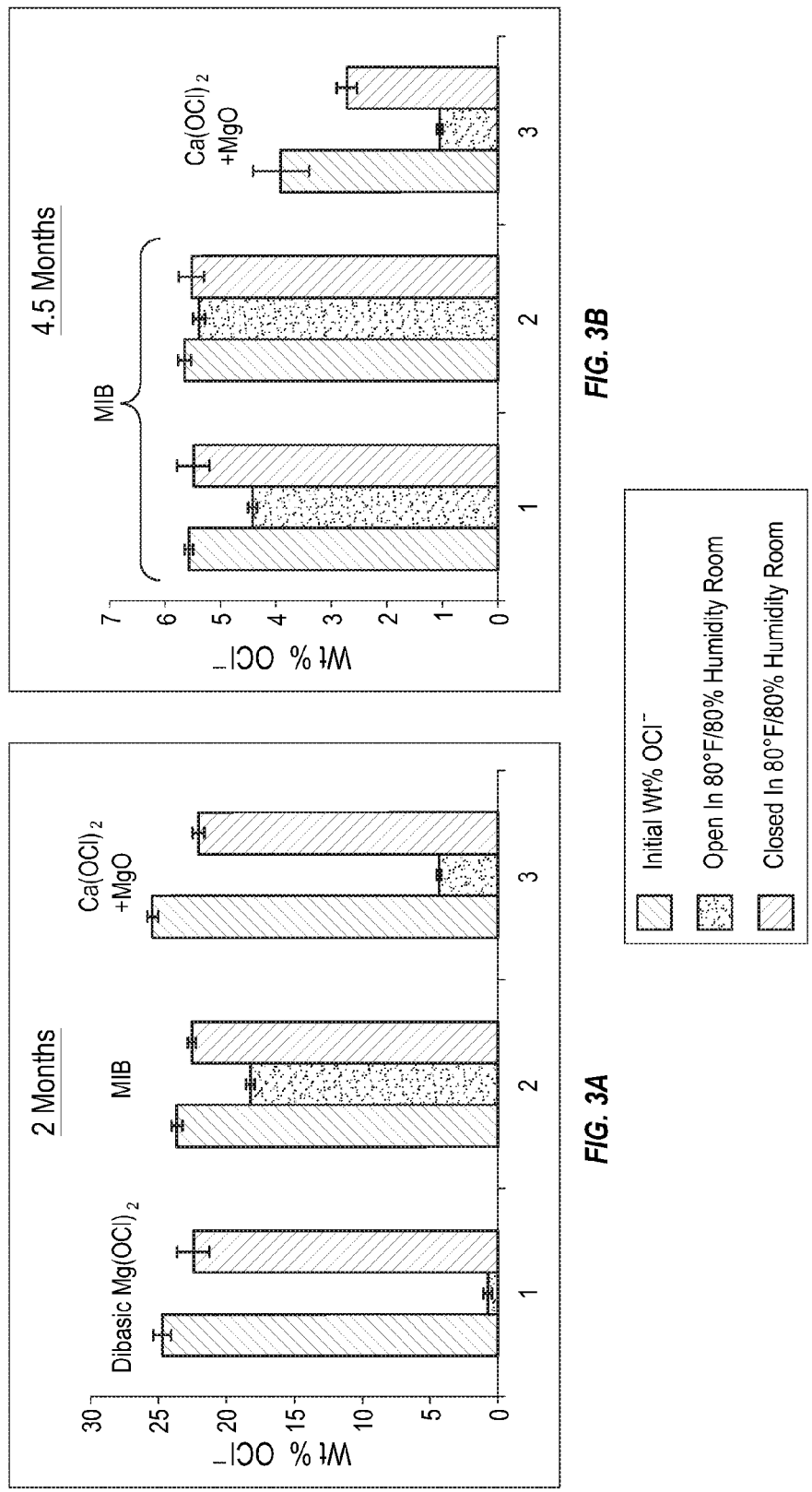
FIG. 3A is a bar chart showing comparative stability in a humid storage environment after 2 months for magnesium intercalated bleach according to the present invention as compared to dibasic magnesium hypochlorite or a mixture of calcium hypochlorite with magnesium oxide.
FIG. 3B is a bar chart showing comparative stability in a humid storage environment after 4.5 months for two magnesium intercalated bleach compositions according to the present invention as compared to a mixture of calcium hypochlorite with magnesium oxide.

In addition to the stability testing described above, the magnesium intercalated bleach compositions were tested for their resistance to humidity (i.e., their ability to resist degradation upon exposure to humidity). The results were compared with the humidity stability of alternative solid hypochlorite releasing products, specifically dibasic magnesium hypochlorite and a mixture of calcium hypochlorite and magnesium oxide. FIG. 3A shows humidity stability data after a period of 2 months storage at a temperature of 80° F. and a relative humidity of 80%. As shown, the initial weight percent hypochlorite was measured. Some samples were stored open, while others were stored closed, and the weight percentage of remaining hypochlorite was measured after the 2 month storage.

As seen, the dibasic magnesium hypochlorite had an initial hypochlorite concentration of about 25% by weight, with a reduction to nearly 0 for the open sample after two months, and a reduction to about 22-23% by weight for the closed sample. The calcium hypochlorite/magnesium oxide mixture had an initial hypochlorite concentration of about 26% by weight, with a reduction to about 5% by weight for the open sample, and a reduction to about 22-23% by weight for the closed sample. The MIB had an initial hypochlorite concentration of about 24% by weight, with a reduction to about 18% by weight for the open sample, and a reduction to about 23% by weight for the closed sample. The MIB exhibits much better resistance to humidity than the other tested alternatives, particularly where the container is left open.

FIG. 3B shows humidity stability data after a period of 4.5 months storage at a temperature of 80° F. and a relative humidity of 80%. The calcium hypochlorite/magnesium oxide mixture had an initial hypochlorite concentration of about 4% by weight, with a reduction to about 1% by weight for the open sample, and a reduction to about 2.5% by weight for the closed sample. Two MIB samples were tested. One MIB sample had an initial hypochlorite concentration of about 5.5% by weight, with a reduction to about 4.5% by weight for the open sample, and no statistical significant reduction for the closed sample. The other MIB sample had an initial hypochlorite concentration of about 5.5% by weight, with no statistical significant reduction for either the closed or open samples.

Figure 4A:
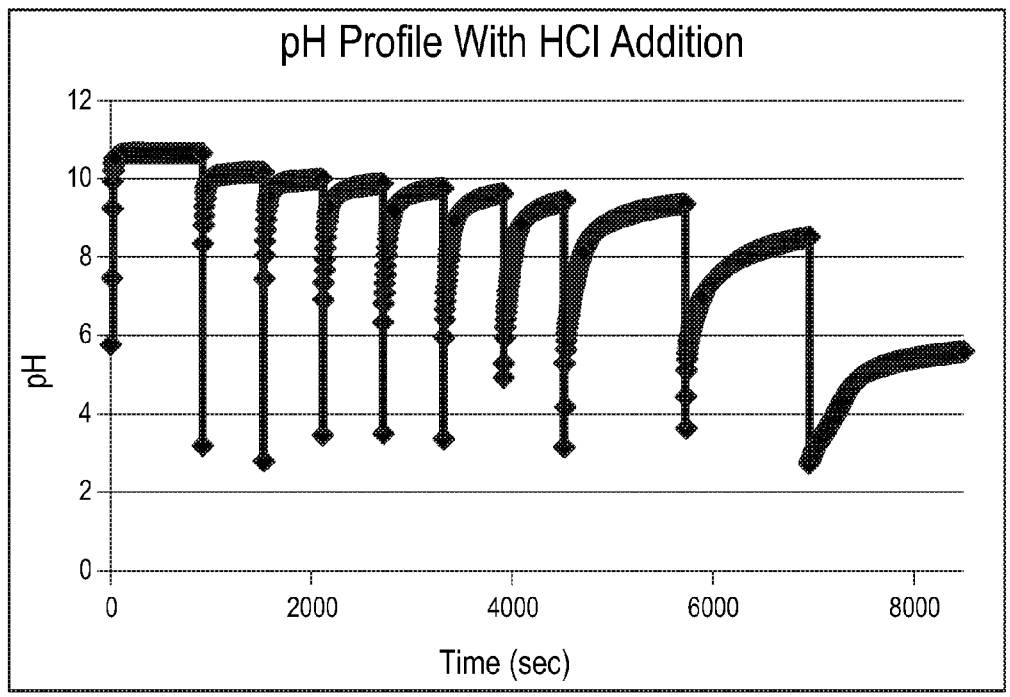
FIG. 4A plots the pH profile of a magnesium intercalated bleach composition with 7.7% available chlorine as HCl is added over time.
Figure 4B:
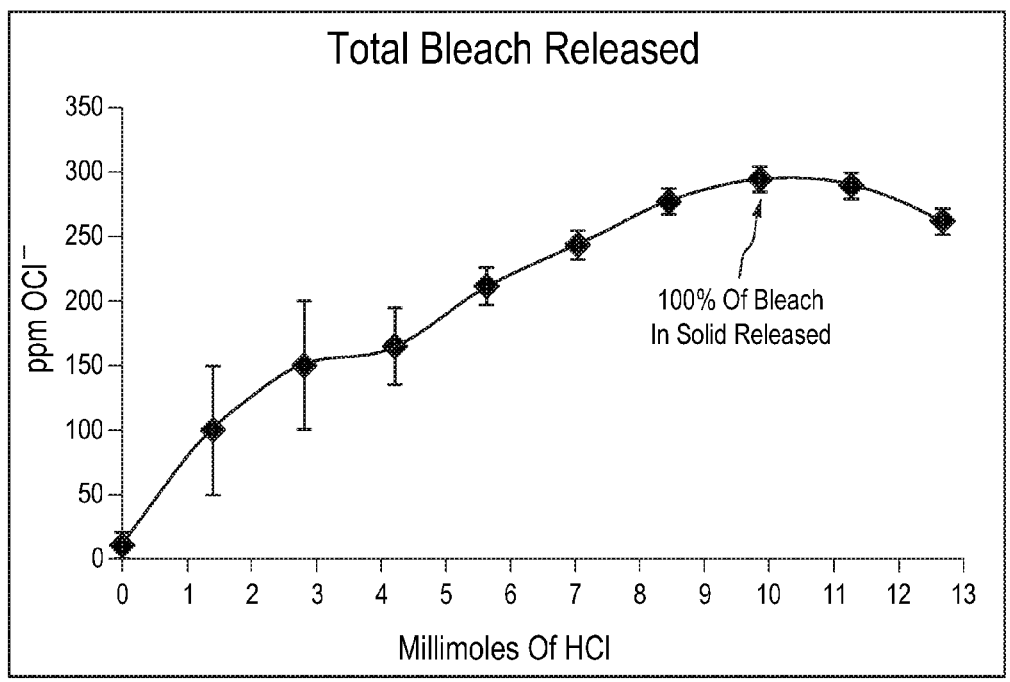
FIG. 4B plots the concentration of hypochlorite ion within the solution of FIG. 4A as a function of millimoles of HCl added.
Figure 5A:
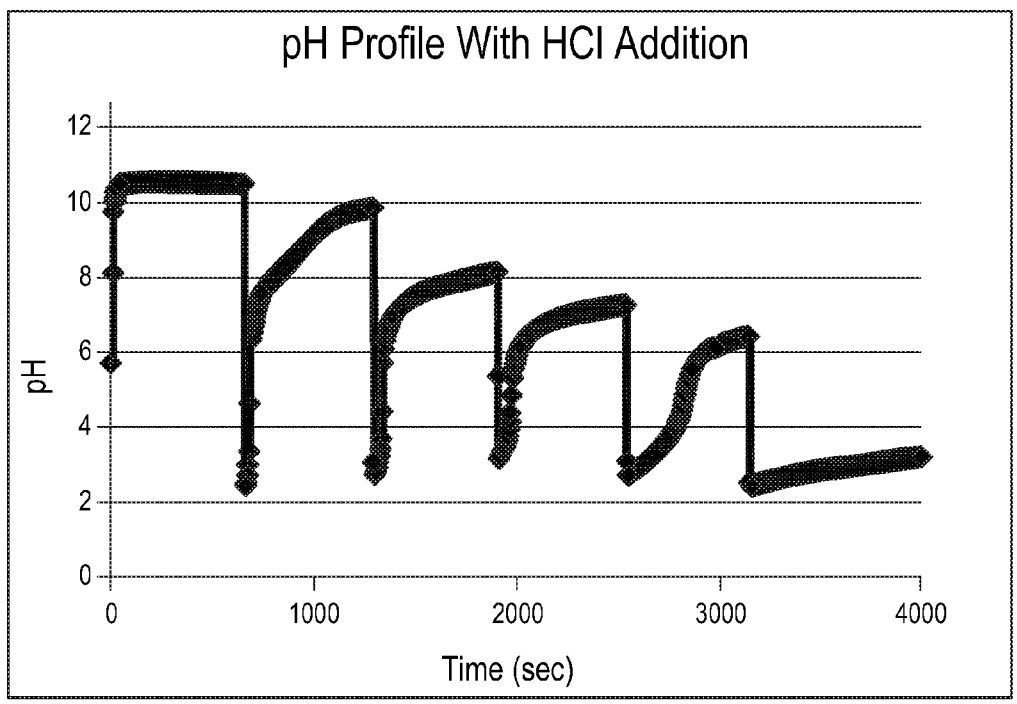
FIG. 5A plots the pH profile of a dibasic magnesium hydroxide bleach composition with 34% available chlorine as HCl is added over time.
Figure 5B:
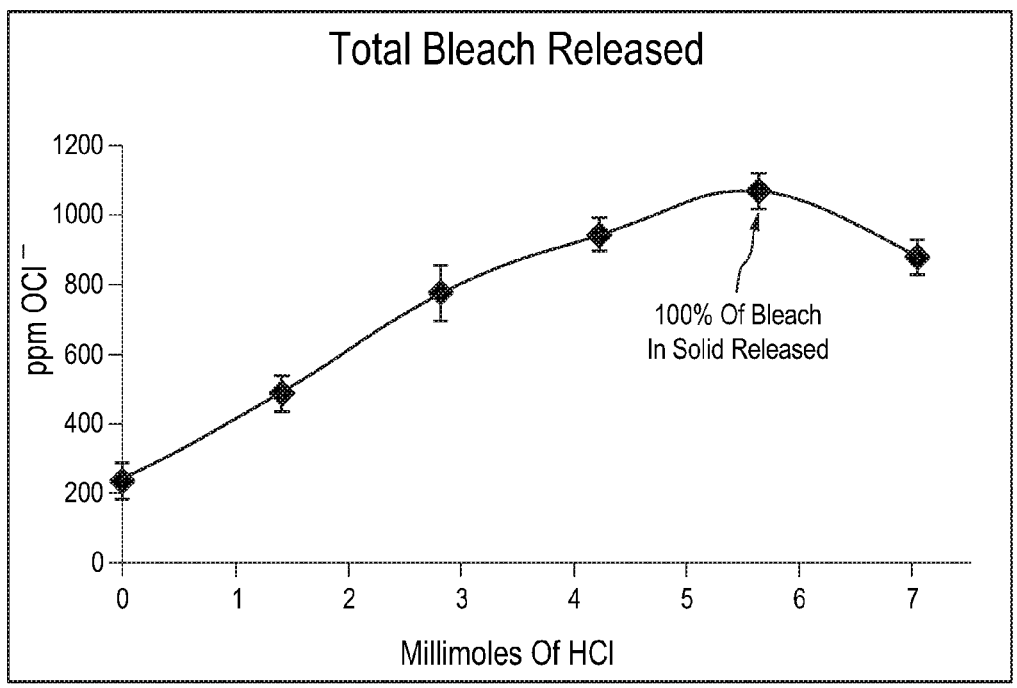
FIG. 5B plots the concentration of hypochlorite ion within the solution of FIG. 5A as a function of millimoles of HCl added.

The buffering characteristics of the MIB compositions, as well as the ability to accelerate release of hypochlorite through addition of an acid were tested. It is believed that the MgO and/or Mg(OH)$_2$ component present within the intercalated bleach compound acts to buffer the pH to a preferred region (e.g., about 8 to about 11.5) for enhanced hypochlorite stability. The results are shown in FIGS. 4A-4B. A comparative example for dibasic magnesium hypochlorite is shown in FIGS. 5A-5B. FIG. 4A plots the pH profile over time as hydrochloric acid (HCl) is added to the MIB aqueous solution at periodic intervals. The MIB compound employed in FIGS. 4A-4B had a concentration of available chlorine of 7.7% by weight (e.g., a Mg to OCl ratio of about 13.9:1 as shown in FIG. 1). The pH profile shows a relatively fast pH recovery, with buffering capability from about 8 to about 11.5.

FIG. 4B plots the concentration of hypochlorite in solution (ppm of OCl) as a function of how many millimoles of HCl are added. As seen, the hypochlorite release is generally linear until all of the hypochlorite within the solid MIB is released (e.g., about 275-300 ppm OCl in FIG. 4B after addition of about 10 millimoles HCl).

FIGS. 5A-5B plot similar data as described above with respect to FIGS. 4A-4B, but for a dibasic magnesium hypochlorite composition including 34% available chlorine by weight. As seen in FIG. 5A, the buffering recovery is significantly slower and less complete than that exhibited by the MIB compositions. In other words, this composition exhibits significantly lower buffering capacity. As such, the dibasic magnesium hypochlorite is not capable of maintaining a relatively high pH for the solution, as are the MIB compositions. Such improved buffering capacity (i.e., the ability to maintain a higher pH for longer) greatly improves the stability of the bleach composition. It is also observed that bleach release is not significantly aided by acid addition in the case of dibasic magnesium hypochlorite, as higher bleach release than that shown in FIG. 5B is actually achieved with plain water.

Figure 6A:
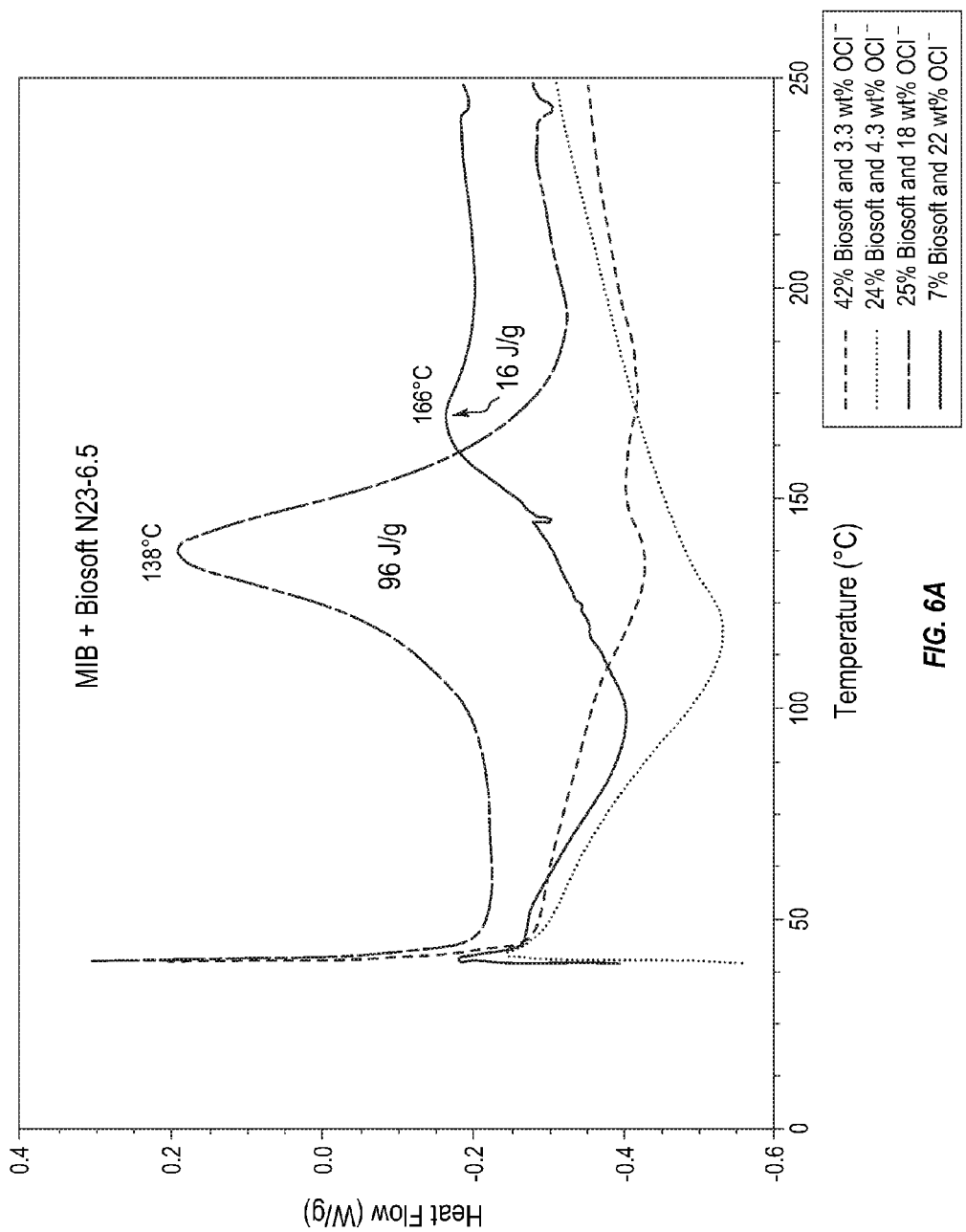
FIG. 6A plots thermodynamic stability data for various MIB compositions formulated with alcohol ethoxylates.

Formulation stability and compatibility with various adjuvants, such as alcohol ethyoxylates (e.g., BIOSOFT N23-6.5), surfactants (e.g., sodium lauryl sulfate, lauryl dimethyl amine oxide), polymers (e.g., SOKANLAN CP 45 granules, ALCOSPERSE 747, propyl vinyl alcohol copolymer film, and quaternary ammonium compounds (e.g., benzyltrimethylammonium chloride, dodecyltrimethylammonium chloride) was tested. FIG. 6A shows differential scanning calorimetry ("DSC") data which can be interpreted as comparative thermodynamic stability data for several different MIB compositions including a wide range of concentrations of the alcohol ethoxylate BIOSOFT N23-6.5. The results indicate that the MIB compositions exhibit excellent compatibility and stability with a wide variety of adjuvants across a wide variety of concentrations.

Figure 6B:
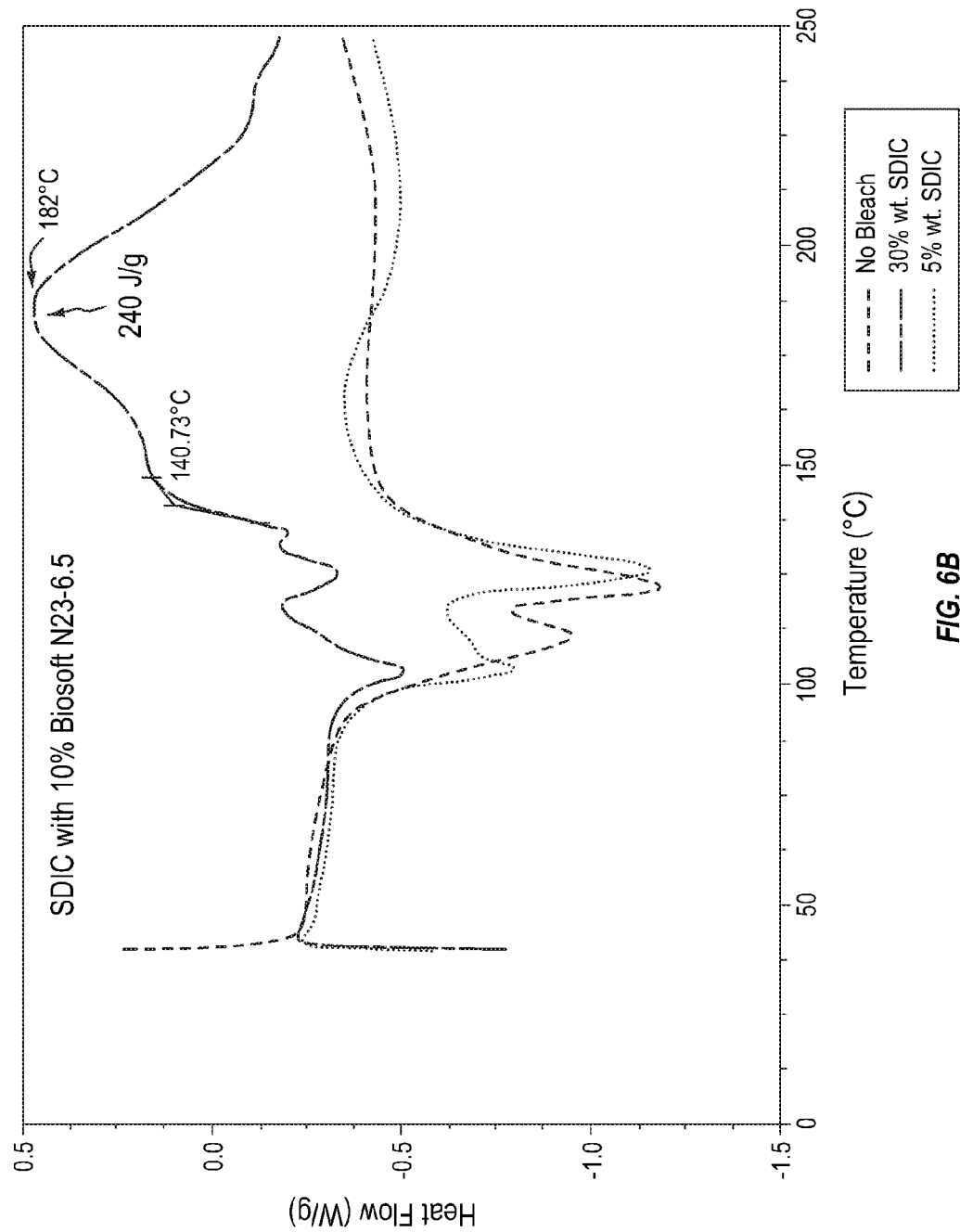
FIG. 6B plots thermodynamic stability data for various comparative sodium dichloroisocyanurate compositions formulated with alcohol ethoxylates.

By way of comparison, FIG. 6B shows less thermodynamic stability for sodium dichloroisocyanurate ("SDIC") compositions with 10% of the alcohol ethoxylate BIOSOFT N23-6.5. The exothermic decomposition reaction of the SDIC and alcohol ethoxylate mixture (17 wt % hypochlorite and 10% alcohol ethoxylate; 240 J/g) is more than an order of magnitude greater than the exothermic decomposition of the comparable MIB composition with alcohol ethoxylate (22 wt % hypochlorite and 7% alcohol ethoxylate; 16 J/g). In fact, even when the amount of alcohol ethoxylate in the mixture with MIB has been more than doubled (18 wt % hypochlorite and 25% alcohol ethoxylate; 96 J/g), the SDIC mixture still shows more than twice the exothermic energy release. Previously, such isocyanurate salts have been regarded as having as good of formula flexibility and compatibility as any chlorine bleach product available. In these cases, the invention MIB shows better formula flexibility and compatibility than SDIC. Furthermore, such isocyanurate salts must be formulated with anhydrous materials, use of sodium hydroxide must be avoided (in fact basic conditions generally must be avoided), the salts cannot be formulated with hydroscopic materials, and the decomposition products of isocyanurate salts include $NCl_3$, which is particularly dangerous and undesirable. The MIB composition does not have these restrictions.

Figure 7A:
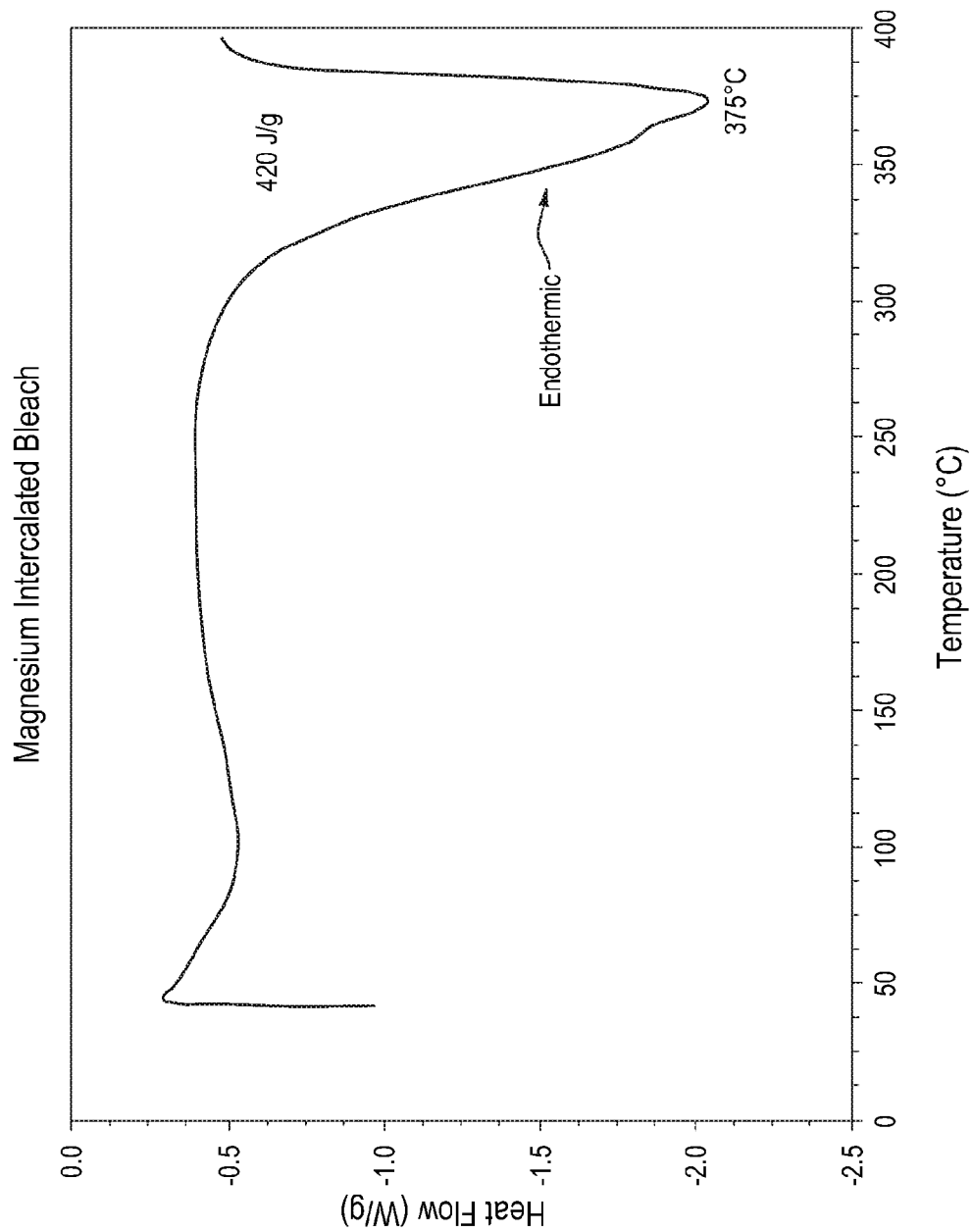
FIG. 7A plots decomposition thermodynamic stability data for an exemplary MIB composition.
Figure 7B:
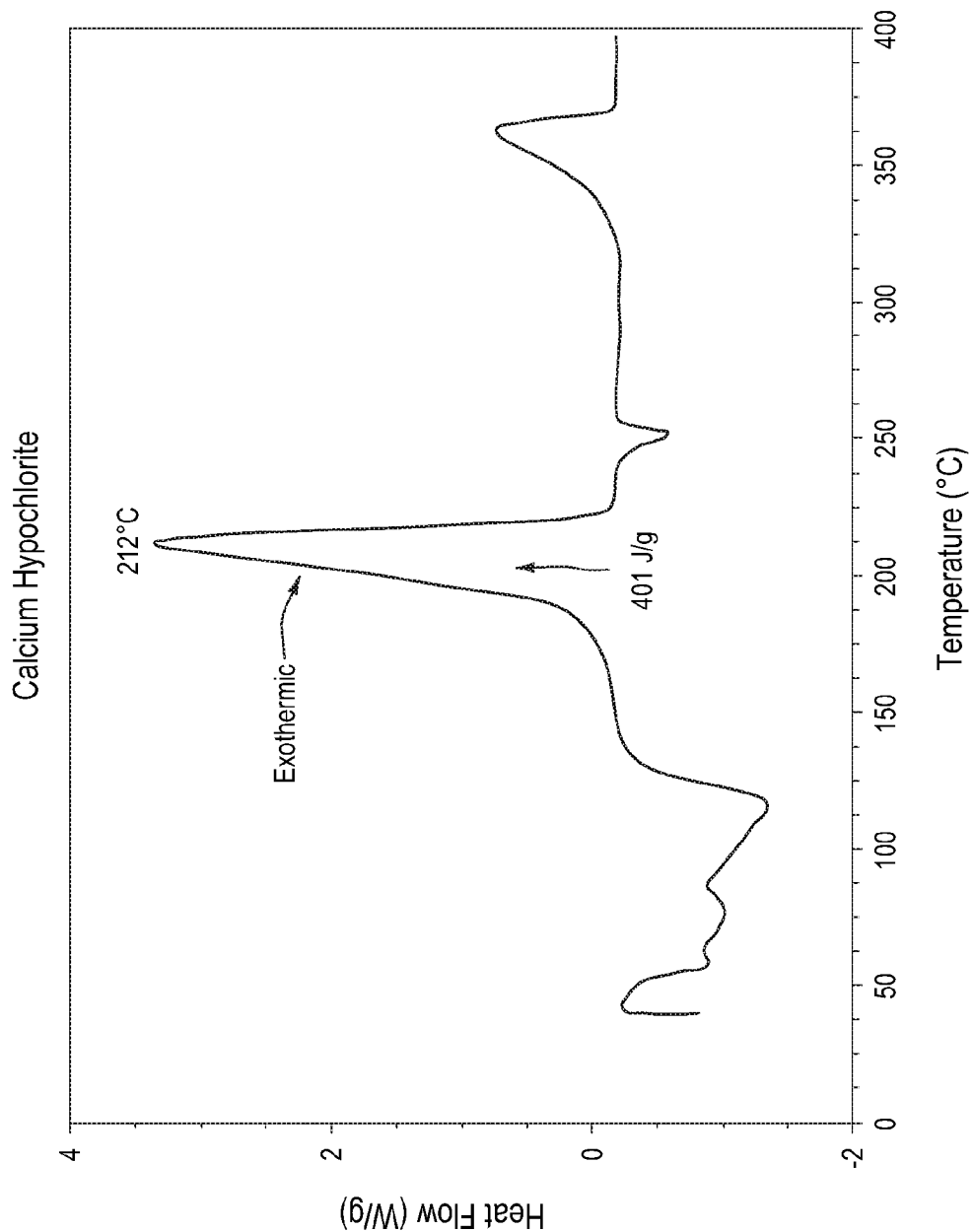
FIG. 7B plots comparative decomposition thermodynamic stability data for calcium hypochlorite.

FIG. 7A shows differential scanning calorimetry ("DSC") data for an exemplary MIB composition, showing an endothermic decomposition reaction at about 375° C., requiring a substantial energy input of 420 J/g. Similar DSC data for calcium hypochlorite is shown in FIG. 7B, for comparison. Calcium hypochlorite shows an exothermic decomposition reaction at about 212° C., giving off energy of 401 J/g, making calcium hypochlorite less desirable relative to the endothermic decomposition pathway of the present invention.

Figure 7C:
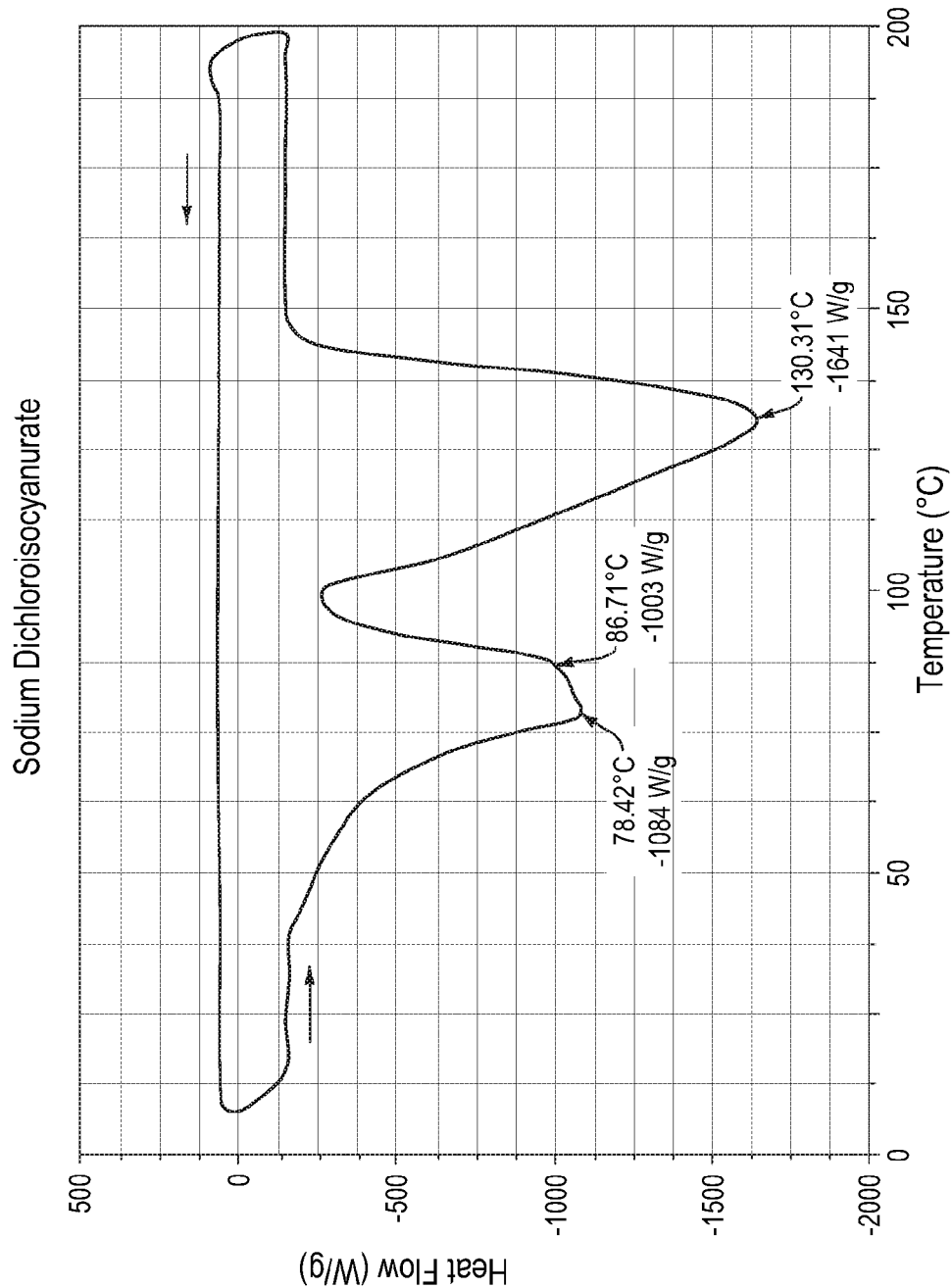
FIG. 7C plots comparative decomposition thermodynamic stability data for sodium dichloroisocyanurate.

FIG. 7C shows DSC data for sodium dichloroisocyanurate, which includes two endothermic reactions, one for loss of each water of hydration. While sodium dichloroisocyanurate exhibits no exothermic decomposition reactions in the temperature range of 10° C. to 200° C., it does form $NCl_3$ byproducts upon decomposition, which is dangerous and undesirable.

Because of the ability to carefully control release of hypochlorite with the intercalated bleach compositions, active bleach can be delivered on demand. For example, any suitable delivery mechanism may be employed, including, but not limited to, solid compositions (e.g., powders, granules, tablets, etc.), packets (e.g., pouches) including a solid composition, or aqueous liquids in which the intercalated bleach is in solution or suspension (e.g., an acid, or chelate, or surfactant, or further dissolution may be used to control hypochlorite concentration and delivery).

Pouches may be formed from polyvinyl alcohol films or other sealable water-soluble or dispersible polymer films. Solid product may be pressed or cast into a tablet, puck, or granule form where the solid solubility is timed and bleach release may be slow and consistent over a given period of time. The composition may be embedded or integrated into a plastic or polymer film, or may be attached to or embedded in a substrate (e.g., polymer, plastic, nonwoven, other fabric, sponge, etc.).

Liquid compositions may be delivered through a trigger sprayer or aerosol delivery system. An embodiment may include a dual chamber bottle or package where two initially separate parts of the composition are contacted with one another immediately prior to dispensing the product. For example, an acidic aqueous solution (e.g., including surfactant, chelating agents, dyes, fragrances, etc.) may be disposed in one chamber of the dual chamber bottle, and this liquid may be drawn through or mixed with the second part of the composition including the intercalated bleach (e.g., a non-woven filtration system), so that the liquid dispensed includes hypochlorite bleach and the actives of the first chamber (e.g., chelating agents, surfactants, dyes, fragrances, etc.). Of course, various adjuvants may be included within one or both parts of such a two part composition, as desired.

By way of summary of the advantageous characteristics of the intercalated bleach compositions as compared to existing alternatives, Table 2 shows relative ratings for various criteria of several solid hypochlorite bleach products, where 5 represents "excellent", 3 represents "fair", and 1 represents "poor". As seen, the inventive MIB compositions are the only products offering "excellent" formula flexibility, low odor, and moisture tolerance. While some products provide better solution clarity or higher levels of available chlorine, the inventive intercalated bleach compounds and compositions provide by far the best combination of high ratings from among the available alternatives.

TABLE 2

| Product | Formula Flexibility | Minimal Odor | Solution Clarity | Bleach Stability | Available Chlorine | Moisture Tolerance | Total Pts |
|---|---|---|---|---|---|---|---|
| Intercalated Bleach | 5 | 5 | 3 | 5 | 3 | 5 | 26 |

TABLE 2-continued

| Product | Formula Flexibility | Minimal Odor | Solution Clarity | Bleach Stability | Available Chlorine | Moisture Tolerance | Total Pts |
|---|---|---|---|---|---|---|---|
| $Ca(OCl)_2$ | 3 | 1 | 3 | 3 | 5 | 3 | 18 |
| $Li(OCl)_2$ | 1 | 1 | 5 | 1 | 3 | 3 | 14 |
| $Na(OCl)_2$ phosphate adduct | 3 | 3 | 5 | 1 | 1 | 3 | 16 |
| Isocyanuric acids | 3 | 1 | 1 | 5 | 5 | 1 | 16 |
| Isocyanurate salts | 3 | 3 | 5 | 5 | 5 | 1 | 22 |
| Dichlorohydantoin | 1 | 3 | 1 | 5 | 5 | 1 | 16 |
| Trichloromelamine | 1 | 1 | 1 | 5 | 5 | 3 | 16 |

The compositions described below are sample solid compositions of $M_x(OCl)_y(O)_m(OH)_n$.

Example 1

Example 1 illustrates a composition of the invention where the magnesium source is magnesium oxide and the bleach source is calcium hypochlorite for $Mg_{13.9}Ca_{0.5}(OCl)O_{12.9}(OH)$.

In Example 1, we dissolve 79.5 grams of calcium hypochlorite (69.2 wt %) in 959.2 grams of water. Mix for 2 minutes. Add 430.5 grams of magnesium oxide over 10 minutes with high shear mixing. Continue mixing for 10 minutes after all magnesium oxide is added. Allow to dry in an open container at room temperature. The product has 7.6% available chlorine.

Example 2

Example 2 illustrates a composition of the invention where the magnesium source is magnesium oxide, the bleach source is calcium hypochlorite and the hypochlorite level is at a high percentage, for $Mg_3Ca_{0.5}(OCl)O_2(OH)$.

In Example 2, we dissolve 51.8 grams of calcium hypochlorite (69.2 wt %) in 186 grams of water. Mix for 2 minutes. Add 60.0 grams of magnesium oxide over 10 minutes with high shear mixing. Continue mixing for 10 minutes after all magnesium oxide is added. Allow to dry in an open container at room temperature. The product has 25.5% available chlorine.

Example 3

Example 3 illustrates a composition of the invention where the magnesium source is magnesium oxide, the bleach source is calcium hypochlorite and the hypochlorite level is at a low percentage, for $Mg_{34.6}Ca_{0.5}(OCl)O_{33.6}(OH)$.

In Example 3, we dissolve 8.9 grams of calcium hypochlorite (69.2 wt %) in 250.6 grams of water. Mix for 2 minutes. Add 120.2 grams of Magnesium oxide over 5 minutes with high shear mixing. Continue mixing for 10 minutes after all magnesium oxide is added. Allow to dry in an open container. The product has 3.7% available chlorine.

Example 4

Example 4 illustrates a composition of the invention where the magnesium source is magnesium hydroxide, the bleach source is calcium hypochlorite and the hypochlorite level is at a high percentage, for $Mg_4Ca_{0.5}(OCl)(OH)_7$.

In Example 4, we dissolve 18.35 grams of calcium hypochlorite (70.7 wt %) in 105.7 grams of water. Mix for 2 minutes. Add 42.8 grams of magnesium hydroxide over 5 minutes with high shear mixing. Continue mixing for 10 minutes after all magnesium hydroxide is added. Allow to dry in an open glass container. The product has 6.4% available chlorine.

Example 5

Example 5 illustrates a composition of the invention where the magnesium source is magnesium hydroxide, the bleach source is calcium hypochlorite and the hypochlorite level is at a low percentage, for $Mg_{33}Ca_{0.5}(OCl)(OH)_{65}$.

In Example 5, we dissolve 2.75 grams of calcium hypochlorite (57.5 wt %) in 98.7 grams of water. Mix for 2 minutes. Add 42.5 grams of magnesium hydroxide over 5 minutes with high shear mixing. Continue mixing for 10 minutes after all magnesium hydroxide is added. Allow to dry in an open container. The product has 1.1% available chlorine.

Example 6

Example 6 illustrates a composition of the invention where the magnesium source is magnesium hydroxide, the bleach source is calcium hypochlorite and the hypochlorite level is at a mid-range percentage, for $Mg_{8.4}Ca_{0.5}(OCl)(OH)_{15.8}$.

In Example 6, we dissolve 17.8 grams of calcium hypochlorite (79 wt %) in 212.6 grams of water. Mix for 2 minutes. Add 95.8 grams of magnesium hydroxide over 5 minutes with high shear mixing. Continue mixing for 10 minutes after all magnesium hydroxide is added. Dry in an open container. The product has 6.7% available chlorine.

Example 7

Example 7 illustrates a composition of the invention where the magnesium source is magnesium oxide, the bleach source is sodium hypochlorite and the hypochlorite level is at a mid-range percentage, for $Mg_{11.9}(OCl)O_{10.9}(OH)$.

In Example 7, magnesium oxide (95.7 grams) was added to 234 grams of sodium hypochlorite (6.4 wt % solution) over 5 minutes with high shear mixing. Continue mixing for 10 minutes after all magnesium oxide is added. Dry in an open container at room temperature. The product has 7.5% available chlorine.

Example 8

Example 8 illustrates a composition of the invention where the magnesium source is magnesium hydroxide, the bleach source is sodium hypochlorite and the hypochlorite level is at a mid-range percentage, for $Mg_{8.4}(OCl)(OH)_{15.8}$.

In Example 8, Magnesium hydroxide (95.8 grams) was added to 230 grams of sodium hypochlorite (6.3 wt % solution) over 5 minutes with high shear mixing. Continue mixing for 10 minutes after all magnesium hydroxide is added. Dry in an open container at room temperature. The product has 2.7% available chlorine.

Without limitation, the following non-limiting examples illustrate implementation of the present invention. Final formula is represented by $M_x(OCl)_y(O)_m(OH)_n$, where M=Mg and Ca. For the purpose of Tables 3-8, $Mg_aCa_b(OCl)_y(O)_m(OH)_n$, where a+b=x.

TABLE 3

| Example | Formula | Reactant 1: Ca(OCl)$_2$ (grams) | Reactant 2: MgO (grams) | Product: Percent Available Chlorine | Quantitative Yield |
|---|---|---|---|---|---|
| 9 | Mg$_3$Ca$_{0.5}$(OCl)(O)$_2$(OH) | 51.8 | 60 | 25.5 | 83.7 |
| 10 | Mg$_{4.5}$Ca$_{0.5}$(OCl)(O)$_{3.5}$(OH) | 51.7 | 91.3 | 19.4 | 88 |
| 11 | Mg$_{5.9}$Ca$_{0.5}$(OCl)(O)$_{4.9}$(OH) | 51.9 | 120 | 18.2 | 99.6 |
| 12 | Mg$_{13.9}$Ca$_{0.5}$(OCl)(O)$_{12.9}$(OH) | 79.5 | 430.5 | 7.6 | 99 |
| 13 | Mg$_{34.6}$Ca$_{0.5}$(OCl)(O)$_{33.6}$(OH) | 8.9 | 120.2 | 3.7 | 91.9 |
| 14 | Mg$_{50.8}$Ca$_{0.5}$(OCl)(O)$_{49.8}$(OH) | 2.6 | 43 | 1.7 | 75 |

Based on final available chlorine levels for different samples, final products are hydrates. Calcium salt impurities in starting calcium hypochlorite materials will be present in final product.

Without limitation, the following non-limiting examples illustrate implementation of the present invention. Final formula is represented by M$_x$(OCl)$_y$(O)$_m$(OH)$_n$, where M=Mg.

TABLE 4

| Example | Formula | Reactant 1: NaOCl (grams) | Reactant 2: MgO (grams) | Product: Percent Available Chlorine | Quantitative Yield |
|---|---|---|---|---|---|
| 15 | M$_{3.1}$(OCl)(O)$_{2.1}$(OH) | 222.4 | 60.4 | 14.84 | 58.1 |
| 16 | M$_{6.2}$(OCl)(O)$_{5.2}$(OH) | 222.3 | 120.3 | 9.98 | 60.2 |
| 17 | M$_{11.9}$(OCl)(O)$_{10.9}$(OH) | 233.8 | 95.9 | 3.12 | n/a |

Based on final available chlorine levels for different samples, final products are hydrates. Sodium salts are present in final product.

Without limitation, the following non-limiting examples illustrate implementation of the present invention. Final formula is represented by M$_x$(OCl)$_y$(OH)$_n$, where M=Mg and Ca. For the purpose of Table Z, Mg$_a$Ca$_b$(OCl)$_y$(OH)$_n$, where a+b=x.

TABLE 5

| Example | Reactant 1: Ca(OCl)$_2$ (grams) | Reactant 2: Mg(OH)$_2$ (grams) | Product: Percent Available Chlorine | Quantitative Yield | Formula |
|---|---|---|---|---|---|
| 18 | 18.4 | 42.77 | 6.43 | 47 | Mg$_4$Ca$_{0.5}$(OCl)(OH)$_7$ |
| 19 | 17.75 | 95.8 | 6.56 | 48 | Mg$_{8.4}$Ca$_{0.5}$(OCl)(OH)$_{15.8}$ |
| 20 | 15.33 | 127.3 | 6.15 | n/a | Mg$_{12.8}$Ca$_{0.5}$(OCl)(OH)$_{24.6}$ |
| 21 | 2.75 | 42.5 | 1.19 | 47 | Mg$_{33}$Ca$_{0.5}$(OCl)(OH)$_{65}$ |

Footnote:
Final products may be hydrates. Calcium salt impurities in starting calcium hypochlorite materials will be present in final product.

Without limitation, the following non-limiting examples illustrate implementation of the present invention.

TABLE 6

| Ingredients | Example 22 Wt. % | Example 23 Wt. % | Example 24 Wt. % | Example 25 Wt. % | Example 26 Wt. % |
|---|---|---|---|---|---|
| Mg$_{12.8}$Ca$_{0.5}$(OCl)(OH)$_{24.6}$ | 50 | | | | |
| Mg$_{8.4}$Ca$_{0.5}$(OCl)(OH)$_{15.8}$ | | 40 | 7 | | |
| Mg$_3$Ca$_{0.5}$(OCl)(O)$_2$(OH) | | | | 10 | |
| Mg$_{4.5}$Ca$_{0.5}$(OCl)(O)$_{3.5}$(OH) | | | | | 15 |
| sodium polyacrylate | 1 | | | | |
| alkyldiphenyloxide disulfonate | 3 | | | | |

TABLE 6-continued

| Ingredients | Example 22 Wt. % | Example 23 Wt. % | Example 24 Wt. % | Example 25 Wt. % | Example 26 Wt. % |
|---|---|---|---|---|---|
| blue dye | 0.1 | | | 0.01 | |
| sodium xylene sulfonate | 0.1 | | 1 | | |
| sodium lauryl sulfate | 0.1 | | | | |
| 10% sulfuric acid | 0.1 | | | | |
| amine oxide | | 13 | | | |
| layered silicate | | 2 | | | |
| cetyldimethylbetaine | | | 5 | | |
| sodium hydroxide (1N) | | | 1 | | |
| citric acid | | | | 45 | |
| sodium bicarbonate | | | | 35 | |
| sodium carbonate | | | | 5 | |
| sodium chloride | | | | 5 | |
| cyclohexane | | | | | 85 |
| water | 45.6 | 45 | 86 | | |

TABLE 7

| Ingredients | Example 27 Wt. % | Example 28 Wt. % | Example 29 Wt. % | Example 30 Wt. % | Example 31 Wt. % |
|---|---|---|---|---|---|
| $Mg_{13.9}Ca_{0.5}(OCl)(O)_{12.9}(OH)$ | 46 | 53 | 27 | 68 | 80 |
| boric acid | 54 | | | | |
| succinic acid | | 47 | | | |
| potassium bisulfate | | | 73 | | |
| benzyltrimethyl ammonium chloride | | | | 32 | |
| dodecyltrimethyl ammonium chloride | | | | | 20 |

TABLE 8

| Ingredients | Example 32 Wt. % | Example 33 Wt. % | Example 34 Wt. % | Example 35 Wt. % | Example 36 Wt. % |
|---|---|---|---|---|---|
| $Mg_{13.9}Ca_{0.5}(OCl)(O)_{12.9}(OH)$ | 93 | | | | |
| $Mg_3Ca_{0.5}(OCl)(O)_2(OH)$ | | 93 | | | |
| $Mg_{12.8}Ca_{0.5}(OCl)(OH)_{24.6}$ | | | 77 | 28 | |
| polyvinyl alcohol film | 7 | 7 | | | |
| dibasic calcium phosphate | | | 23 | | |
| alkylnapthalene sulfonate | | | | 3 | |
| Sodium polyacrylate | | | | | 50 |
| water | | | | 69 | |
| | | | | 55 | |

TABLE 9

| Ingredients | Example 37 Wt. % | Example 38 Wt. % | Example 39 Wt. % | Example 40 Wt. % | Example 41 Wt. % |
|---|---|---|---|---|---|
| $Mg_{13.9}Ca_{0.5}(OCl)(O)_{12.9}(OH)$ | 93.5 | 50 | | | |
| $Mg_3Ca_{0.5}(OCl)(O)_2(OH)$ | | | 93 | 50 | 33 |
| alcohol ethoxylate | 6.5 | 50 | 7 | 50 | |
| Sodium polyacrylate | | | | | 67 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A composition comprising:
(a) a bleach compound having the formula:

$$M_x(OCl)_y(O)_m(OH)_n$$

wherein M is selected from the group consisting of magnesium, calcium and mixtures thereof;
wherein x and y independently equal any number greater than or equal to 1;
wherein m and n independently equal any number greater than or equal to 0, but m and n are not both 0; and
wherein x is $\geq 3y$; and
(b) a silicate.

2. The composition of claim 1, wherein M is magnesium.

3. The composition of claim 1, wherein M is calcium.

4. The composition of claim 1, further comprising a surfactant.

5. The composition of claim 1, further comprising an acid.

6. The composition of claim 1, further comprising one or more alkaline earth metal salts or alkali metal salts.

7. The composition of claim 6, wherein alkali metal salts or alkaline earth metal salts are selected from the group consisting of alkaline earth oxides, alkaline earth hydroxides, alkaline earth carbonates, alkaline earth bicarbonates, alkaline earth chlorides, alkali chlorides, alkali carbonates, alkali bicarbonates, and combinations thereof.

8. The composition of claim 7, wherein alkali or alkaline earth salts are selected from the group consisting of magnesium oxide, magnesium hydroxide, magnesium chloride trihydroxide, magnesium chloride pentahydroxide, magnesium carbonate, magnesium chloride, calcium oxide, calcium hydroxide, calcium carbonate, calcium chloride, sodium chloride, sodium carbonate, sodium bicarbonate, and combinations thereof.

9. The composition of claim 1, wherein $2m+n \geq 5y$.

10. The composition of claim 1, wherein $x=0.5y+m+0.5n$.

11. The composition of claim 1, wherein x, y, m, and n are integers.

12. The composition of claim 1, wherein the bleach compound has a range of available chlorine from about 3% to about 25%.

13. The composition of claim 1, wherein the bleach compound is a hydrate.

14. The composition of claim 1, further comprising at least one member selected from the group consisting of builders, surfactants, water soluble polymers, acids, fillers, diluents, desiccants, buffers, solid processing aids, preservatives, colorants, anti-corrosion inhibitors, dyes, fragrances, hydrotropes, polymer dispersants, chelating agents, water-swellable polymers, disinfectants, antimicrobials, essential oils, enzymes, and combinations thereof.

15. The composition of claim 1, wherein the composition is a solid.

16. The composition of claim 15, wherein the composition is in powder, granule, or tablet form.

17. A composition comprising:
(a) a bleach compound having the formula:

$$Mg_x(OCl)_y(O)_m(OH)_n$$

wherein x and y independently equal any number greater than or equal to 1;
wherein m and n independently equal any number greater than or equal to 0, but m and n are not both 0; and
wherein x is $\geq 3y$; and
(b) a boric acid.

18. A composition comprising:
(a) a bleach compound having the formula:

$$Mg_x(OCl)_y(O)_m(OH)_n$$

wherein x and y independently equal any number greater than or equal to 1;
wherein m and n independently equal any number greater than or equal to 0, but m and n are not both 0; and
wherein x is $\geq 3y$; and
(b) a polyacrylate.

19. The composition of claim 18, further comprising an acid.

20. The composition of claim 18, wherein the composition is a solid.

* * * * *